United States Patent
Negroni et al.

(10) Patent No.: US 9,518,271 B2
(45) Date of Patent: Dec. 13, 2016

(54) LENTIVIRAL-BASED VECTOR AND ITS USE IN DIRECTED EVOLUTION OF GENOMIC REGIONS, GENES AND POLYNUCLEOTIDES

(75) Inventors: Matteo Negroni, Strasbourg (FR); Sarah Gallois-Montbrun, Ville d'Avray (FR); Paola Rossolillo, Strasbourg (FR); Vincenzo Di Bartolo, Antony (FR); Gilles Uze, Montpellier (FR); Etienne Simon-Loriere, State College, PA (US); Roland Marquet, Illkirch-Graffenstaden (FR); Valérie Vivet-Boudou, Strasbourg (FR)

(73) Assignees: CENTRE NATIONAL DE LA RECHERCHE SCIENTIFIQUE, Paris (FR); UNIVERSITE PIERRE ET MARIE CURIE (PARIS 6), Paris (FR)

( * ) Notice: Subject to any disclaimer, the term of this patent is extended or adjusted under 35 U.S.C. 154(b) by 475 days.

(21) Appl. No.: 13/509,027

(22) PCT Filed: Nov. 10, 2010

(86) PCT No.: PCT/EP2010/067246
§ 371 (c)(1),
(2), (4) Date: Jul. 5, 2012

(87) PCT Pub. No.: WO2011/058081
PCT Pub. Date: May 19, 2011

(65) Prior Publication Data
US 2012/0264616 A1  Oct. 18, 2012

(30) Foreign Application Priority Data
Nov. 10, 2009 (EP) .................... 09290856

(51) Int. Cl.
*C40B 20/00* (2006.01)
*C12N 15/86* (2006.01)
*C12N 7/00* (2006.01)
*C12N 15/49* (2006.01)

(52) U.S. Cl.
CPC ............... *C12N 15/86* (2013.01); *C12N 7/00* (2013.01); *C12N 2740/16043* (2013.01); *C12N 2740/16062* (2013.01)

(58) Field of Classification Search
None
See application file for complete search history.

(56) References Cited

U.S. PATENT DOCUMENTS

2001/0044149 A1   11/2001  Olsen

OTHER PUBLICATIONS

Dull et al., "A Third-Generation Lentivirus Vector with a Conditional Packaging System", Journal of Virology, vol. 72, No. 11, p. 8463-8471 (1998).*
Das et al., "Viral Evolution as a Tool to Improve the Tetracycline-regulated Gene Expression System", The Journal of Biological Chemistry, vol. 279, No. 18, p. 18776-18782 (2004).*
Arhel et al., "HIV-1 DNA Flap formation promotes uncoating of the pre-integration complex at the nuclear pore", The EMBO Journal, vol. 26, p. 3025-3037 (2007).*
Dull et al. "A Third-Generation Lentivirus Vector with a Conditional Packaging System", Journal of Virology, vol. 72, No. 11, p. 8463-8471 (1998).*
Das et al., "Viral Evolution as a Tool to Improve the Tetracycline-regulated Gene Expression System", The Journal of Biological Chemistry, vol. 279, No. 18, issue of Apr. 30, 2004, pp. 18776-18762, XP-002373382.
Shivange et al., "Advances in Generating Functional Diversity for Directed Protein Evolution", Current Opinion in Chemical Biology, vol. 13, No. 1, pp. 19-25, 2009, XP002577095.
Simon-Loriere et al., "Molecular Mechanisms of Recombination Restriction in the Envelope Gene of the Human Immunodeficiency Virus", Plos Pathogens, vol. 5, No. 5, E1000418, May 2009, XP002577096.
Zennou et al., "HIV-1 Genome Nuclear Import Is Mediated by a Central DNA Flap", Cell, vol. 101, pp. 173-185, Apr. 14, 2000, XP-002168292.
European Search Report dated Apr. 12, 2010, from corresponding EP application.

* cited by examiner

*Primary Examiner* — Antonio Galisteo Gonzalez
(74) *Attorney, Agent, or Firm* — Young & Thompson

(57) ABSTRACT

A method of directing evolution of a target polynucleotide of interest for obtaining variants of this target polynucleotide, a method to generate genetic variability by preparing a cell library, and a method to isolate or to screen variants of a polynucleotide or variants of a protein able to impact the phenotype of a cell or to confer a desired phenotype to target cells, and to identify theses polynucleotide variants or protein variants responsible for this phenotype are described.

23 Claims, 14 Drawing Sheets

A.

B.

C.

D.

A.

TGGAAGGGCTAATTCACTCCCAAAGAAGACAAGATATCCTTGATCTGTGGATCTACCACACACAA
GGCTACTTCCCTGATTAGCAGAACTACACACCAGGGCCAGGGGTCAGATATCCACTGACCTTTGG
ATGGTGCTACAAGCTAGTACCAGTTGAGCCAGATAAGGTAGAAGAGGCCAATAAAGGAGAGAACA
CCAGCTTGTTACACCCTGTGAGCCTGCATGGGATGGATGACCCGGAGAGAGAAGTGTTAGAGTGG
AGGTTTGACAGCCGCCTAGCATTTCATCACGTGGCCCGAGAGCTGCATCCGGAGTACTTCAAGAA
CTGCTGATATCGAGCTTGCTACAAGGGACTTTCCGCTGGGGACTTTCCAGGGAGGCGTGGCCTGG
GCGGGACTGGGGAGTGGCGAGCCCTCAGATCCTGCATATAAGCAGCTGCTTTTGCCTGTACTGG
GTCTCTCTGGTTAGACCGGATCTGAGCCTGGGAGCTCTCTGGCTAACTAGGGAACCCACTGCTTA
AGCCTCAATAAAGCTTGCCTTGAGTGCTTCAAGTAGTGTGTGCCCGTCTGTTGTGACTCTGGT
AACTAGAGATCCCTCAGACCCTTTTAGTCAGTGTGGAAAAATCTCTAGCA (SEQ ID NO:5)

B.

TGGAAGGGCTAATTCACTCCCAAGGAAGACAAGATATCCTTGATCTGTGGATCTACCACACACA
AGGCTACTTCCCTGATTGGCAGAACTACACACCAGGGCCAGGGATCAGATATCCACTGACCTTT
GGATGGTGCTACAAGCTAGTACCAGTTGAGCAAGAGAAGGTAGAAGAAGCCAATGAAGGAGAGA
ACACCCGCTTGTTACACCCTGTGAGCCTGCATGGGATGGATGACCCGGAGAGAGAAGTATTAGA
GTGGAGGTTTGACAGCCGCCTAGCATTTCATCACATGGCCCGAGAGCTGCATCCGGAGTACTTC
AAGAACTGCTGACATCGAGCTTGCTACAAGGGACTTTCCGCTGGGACTTTCCAGGGAGGCGTG
GCCTGGGCGGGACTGGGGAGTGGCGAGCCCTCAGATGCTGCATATAAGCAGCTGCTTTTGCTT
GTACTGGGTCTCTCTGGTTAGACCGGATCTGAGCCTGGGAGCTCTCTGGCTAACTAGGGAACCC
ACTGCTTAAGCCTCAATAAAGCTTGCCTTGAGTGCTTCAAGTAGTGTGTGCCCGTCTGTTGTGT
GACTCTGGTAACTAGAGATCCCTCAGACCCTTTTAGTCAGTGTGGAAAAATCTCTAGCA
(SEQ ID NO :6)

Fig. 13

LENTIVIRAL-BASED VECTOR AND ITS USE IN DIRECTED EVOLUTION OF GENOMIC REGIONS, GENES AND POLYNUCLEOTIDES

FIELD OF THE INVENTION

The present invention concerns a new method of directing evolution of a target polynucleotide of interest (genomic region, gene, coding sequence or any polynucleotide) for obtaining variants of this target polynucleotide that confer a desired phenotype to target cells, especially to mammalian cells, in particular human cells. In particular, the present invention concerns a method to generate genetic variability by preparing a cell library as well as a method to isolate variants of a polynucleotide or variants of a protein able to impact the phenotype of a cell, and to identify theses polynucleotide variants or protein variants responsible for this phenotype.

BACKGROUND OF THE INVENTION

Randomised mutagenesis of genes of interest has recently deserved increased attention. In the existing prior art, a library of mutated genes is first generated and then screened for the presence of mutants possessing a given property either in vitro or, if possible, through genetic screening in bacterial cells. However, when eukaryotic proteins are targeted, the properties observed in vitro for a given mutant often do not result in the desired phenotype when introduced in the eukaryotic cell. For example, it has been shown that mutants isolated for their ability to carry out a specific enzymatic activity, as the phosphorylation of thymidine residues or thymidine kinase (TK) activity in vitro or in bacteria, proved to be inefficient to confer a $TK^+$ phenotype to TK-human cells in culture.

To date, only one system, the tetracycline-regulated gene expression system (Tet system), that benefits from the propensity of retroviruses to promote genetic diversity for molecular evolution experiments has been demonstrated (Das A. T., Zhou X., Vink M., Klaver B., Verhoef K., et al. (2004) J. Biol. Chem., 279: 18776-82). In Das et al., replication-competent viruses (functional viruses) were constructed, and genomic expression was driven by the Tet system. By selecting for the faster replicating variants, an improved Tet system was selected. However, in the approach adopted by Das et al., selection was necessarily coupled to viral replication capacity, and its applications extremely limited.

However, it is also known in the art that the use of functional viruses, and more particularly human immunodeficiency virus (HIV), presents several drawbacks, the most important of which are (a) the cytotoxicity of viral infection that constitutes a major obstacle to subsequent selection of cells with the desired phenotype, (b) the limited availability of "free" room in the viral genome to harbour exogenous genes, and (c) the impossibility of blocking the infectious process when desired.

Another approach is to generate a bank of mutated genes by degenerated polymerase chain reaction (PCR), followed by insertion of the thereby generated library in bacteria. A common step after the generation of the library is then the screening for the mutant possessing the desired phenotype, generally in vitro or, when possible, in bacteria having the appropriate genetic background for such screening. However, when the mutated gene is intended to confer a desired phenotype to a human cell, these pre-screening tests often lead to the isolation of mutants that actually do not confer the desired phenotype to the human cell. Direct screening of the library in the human cell by inserting the genes by transfection is also made difficult by the low efficiency of generation of stable clones by this method, which dramatically reduces the complexity of the library, and by the problem that this procedure generates, of the insertion of multiple copies of the gene in the cell genome. This hampers clonal screening. Insertion of the library in lentiviral vectors allows clonal screening quite easily, instead. However, transposing the library from the bacteria to the lentiviral vectors also suffers from a drastic low efficiency that reduces the complexity of the library. Generating the library directly in these vectors, instead, bypasses this problem.

Therefore, there is a need for a system or a method for molecular evolution that avoids at least some of these drawbacks. This is the purposes of the method hereafter disclosed.

(i) positive selection on a negative genetic background, (ii) negative selection on a negative genetic background, and (iii) positive selection for a secreted protein.

Figure 8:
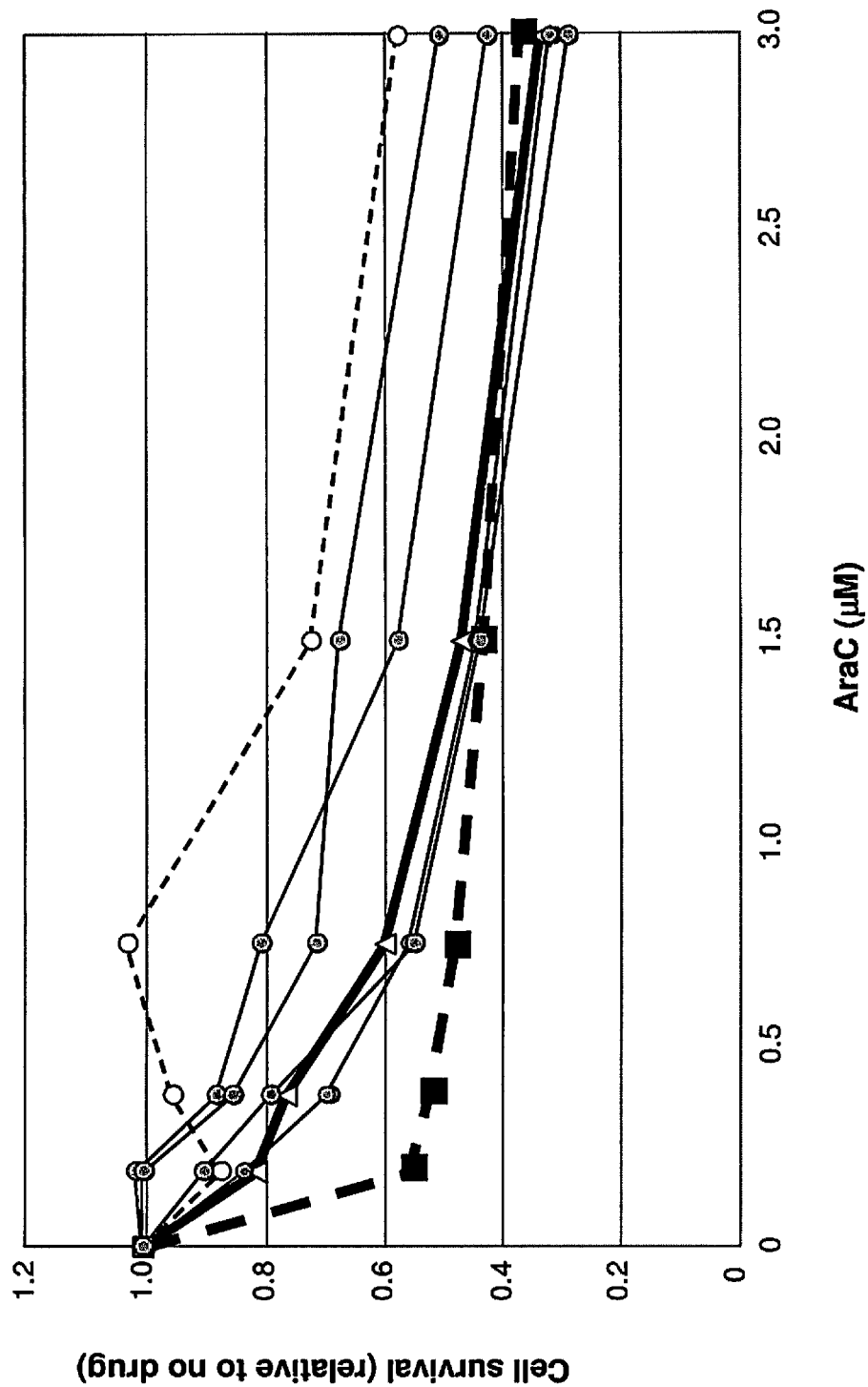

FIG. 8 discloses the cell survival with regard to increasing concentrations of AraC (μM) in presence of the wild type dCK gene (white triangles and solid thick curve) or variants containing point mutations or deletion in the dCK gene (other curves). Each plot represents the average of three independent experiments. Thin solid lines and grey circles: variants giving a death rate comparable to wt dCK one; dotted thin line and white circles: variant giving a death rate lower than the wt dCK one; Dotted thick line and black squares: variant giving a death rate higher than the dCK one.

Figure 9:
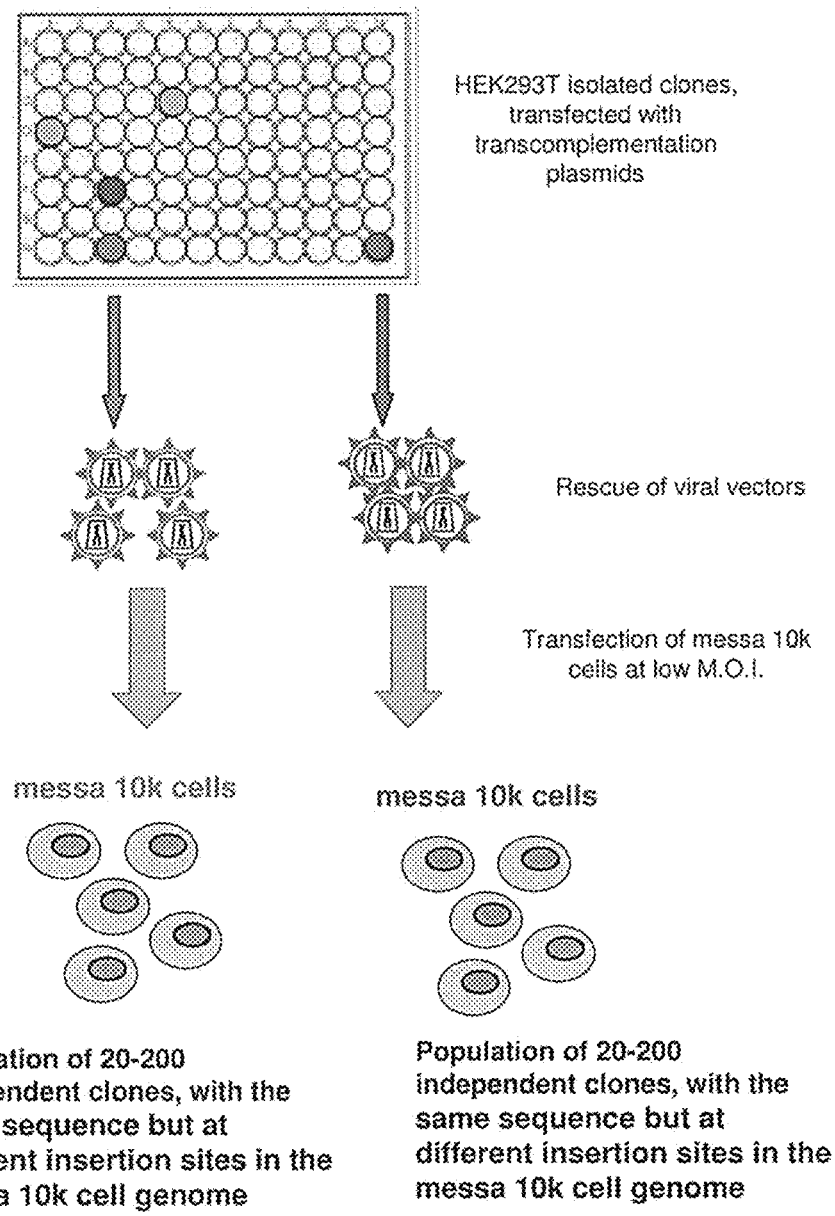

FIG. 9 is a diagram illustrating the screening methodology implemented to identify Messa 10K cells transduced with dCK variants more sensitive to Gemcitabine than wild type Messa 10K cells.

Figure 10:
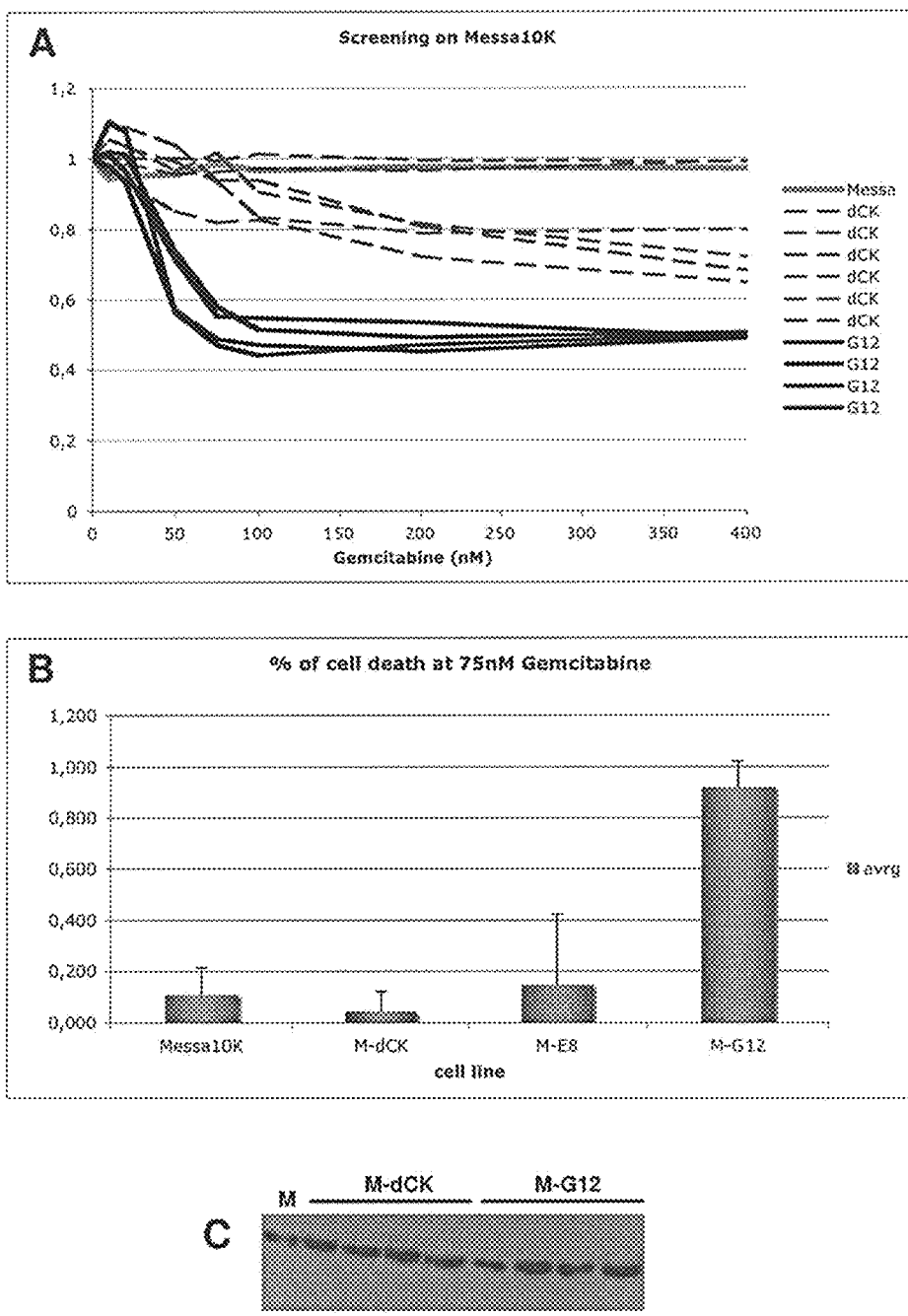

FIG. 10 discloses (A) the cell survival with regard to increasing concentrations of Gemcitabine (nM) in untransduced Messa 10K cells (grey solid line), in presence of the wild type dCK gene (large dashed lines) or in presence of dCK G12 variants gene (black solid lines); (B) the survival of Messa 10K cells in presence of 75 nM Gemcitabine in untransduced Messa 10K cells (Messa10K), in Messa 10K cells transduced with a viral vector carrying a wild type dCK gene (M-dCK), in Messa 10K cells transduced with a viral vector carrying the E8 variant dCK gene with mutations G>A 739 et C>A 745 (M-E8) or in Messa 10K cells transduced with a viral vector carrying the G12 variant dCK gene (M-G12), and (C) Western Blot to detect dCK expression on cell lysates, using a polyclonal rabbit antibody; M: untransduced Messa10K cells; M-dCK: Messa10K transduced with a vector carrying the wt dCK gene (4 independent populations); M-G12: Messa10K transduced with a vector carrying the G12 mutant (4 independent populations).

Figure 11:
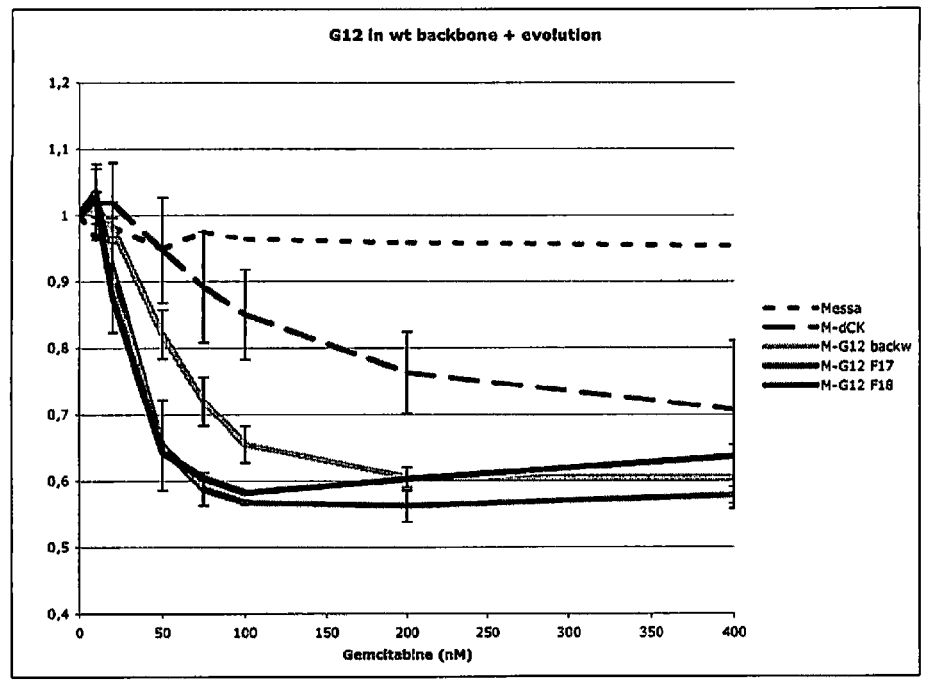

FIG. 11 discloses the cell survival with regard to increasing concentrations of Gemcitabine (nM) in untransduced Messa10K cells (small dashed line), in Messa10K cells transduced with a vector carrying the wt dCK gene (large dashed line; n=5), in Messa10K cells transduced with a vector carrying the sequence of the dCK G12 variant re-inserted in a wild-type backbone (light grey line; n=5), in Messa10K cells transduced with a vector rescued from the 293T-G12-F16 cell line (dark grey line; n=5) and in Messa10K cells transduced with a vector rescued from the 293T-G12-F17 cell line (solid black line; n=5).

Figure 12:
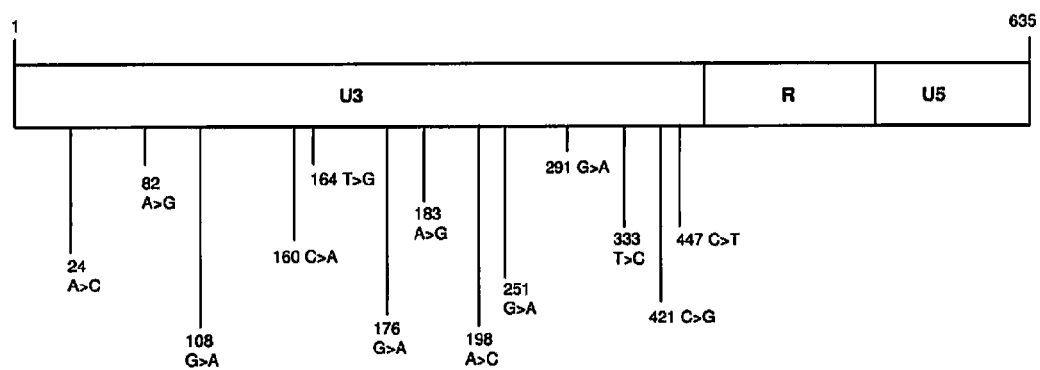

FIG. 12 is a diagram representing the LTR region of a lentiviral vector obtained at the $8^{th}$ generation, and showing the mutations obtained in the U3 region of these evolved vectors.

FIG. 13 represents (A) the sequence of the wild type LTR of HIV-1 (SEQ ID NO:5) and (B) the sequence of the mutated LTR as defined in SEQ ID NO:6. Mutations are underlined, and numbered according to the +1 nucleotide of SEQ ID NO:5.

DETAILED DESCRIPTION OF THE INVENTION

In order to answer some of the above-mentioned needs, the present application describes a method, which is based on the insertion of at least one target polynucleotide in retroviral-derived vectors, and on the abilities of the viral replication machinery to drive the evolution of these at least one target polynucleotide and to generate a library of variants directly in the appropriate vector, for delivery to target cells.

Thus, the present invention relates to a cell culture (in vitro) method for generating genetic diversity in the nucleotide sequence of a target polynucleotide, comprising:
a) providing parental (P) replication-defective lentiviral particles comprising a genetic material encapsidated in said particles, wherein said genetic material comprises the regulatory elements necessary for the transfer, transcription and optionally expression of said genetic material in the genome of a cell host and at least one target polynucleotide;
b) transducing producer cells with the parental replication-defective lentiviral particles of step a), optionally in the presence of a mutagen, to obtain parental cells;
c) transcomplementing the parental producer cells of step b) with viral proteins necessary for the production of a first filial generation of replication-defective lentiviral particles (F1);
d) collecting the first filial generation of replication-defective lentiviral particles (F1);
e) repeating, n consecutive times, with n being 1 or more, the at least three following steps:
  e1) transducing fresh producer cells with the immediately previous filial generation of replication-defective lentiviral particles, optionally in the presence of a mutagen, thereby obtaining a Fn filial cell generation;
  e2) transcomplementing the Fn producer cells of step e1) with viral proteins necessary for the production of a n+1 generation of replication-defective lentiviral particles (Fn+1); and
  e3) collecting the n+1 generation of replication-defective lentiviral particles (Fn+1);
thereby obtaining a population of replication-defective lentiviral particles of the n+1 filial generation, wherein said replication-defective lentiviral particles contain the target polynucleotide or a nucleotide variant of the target polynucleotide.

The method of the invention described in relation to lentiviral particles would more broadly concern retroviral particles.

The first step in the method is to provide parental replication-defective lentiviral particles which comprise the genetic material necessary for the remaining of the method. A lentiviral particle is constituted of both proteins and a genetic material that is encapsidated into these proteins. Particles are made of viral envelope proteins (encoded by an env gene) as well as structural proteins (encoded by the gag gene). Inside the particle, a viral core (or capsid) is found, formed of three enzymes (encoded by the pol gene) i.e., the reverse transcriptase, the integrase and the protease, and of genetic material.

The genetic material is present in the particle under the form of two molecules of RNA. Each molecule of RNA, which can be the same or different, comprises regulatory elements necessary for the transfer, transcription and optionally expression of the genetic material into the genome of a cell host and at least one target polynucleotide. The regulatory elements necessary for the transfer, transcription and optionally expression of the genetic material in the genome of a cell host are well known in the art and comprises LTR (both in 5' and 3'), the encapsidation sequence (named psi or ψ) which is a sequence necessary for the encapsidation of the RNA molecules when the particle is formed, the primer-binding site (PBS), the PPT (polypurine tract) sequence, and the RRE (Rev-responsive element), a sequence required for the binding of viral Rev protein and efficient packaging of the genetic material in the particles.

The expression "LTR" (long-terminal repeat) refers to a nucleotide sequence found in retroviral (preferably lentiviral) DNA at both ends of the reverse transcription product. An example of LTR is the one of HIV-1 as defined in SEQ ID NO: 5. In this sequence, the region U3 is from nucleotides 1 to 455, the R region is from nucleotides 456 to 551 and the U5 region is from nucleotides 552 to 635. LTRs drive the expression of genomic and subgenomic RNAs, both in retroviruses and in retroviral-derived vectors (preferably lentivirus or lentiviral-derived vectors). LTRs are partially transcribed into an RNA intermediate, followed by reverse transcription into complementary DNA (cDNA) and ultimately into dsDNA (double-stranded DNA) with new full LTRs. The LTRs also mediate integration of the retroviral DNA via an LTR-specific transposase called integrase into the host cell's chromosomal DNA. As is known in the art, this is the basic mechanism of integration used by the human immunodeficiency virus (HIV).

The expression "3' LTR" refers to a 3' retroviral or lentiviral long terminal repeat, which may or may not be modified from its corresponding native 3' LTR (i.e., existing in the wild type retrovirus) by deleting and/or mutating endogenous sequences and/or adding heterologous sequences. The expression "5' LTR" refers to a 5' retroviral or lentiviral long terminal repeat, which may or may not be modified from its corresponding native 5' LTR by deleting and/or mutating endogenous sequences and/or adding heterologous sequences. LTRs may be natural or synthetic.

In an advantageous embodiment of the invention, the genetic material also comprises sequences that have been identified to be involved in the improvement of nuclear import of the reverse transcribed DNA and thus in the improvement of integration into the host cell: cis-acting cPPT and CTS sequences forming the so-called flap sequence (Zennou V. et al. (2000) Cell, 101, 173-185). As will be known by a skilled person in the art, a plasmid containing these cPPT-CTS sequences is particularly useful to transduce non-dividing cells. In a particular embodiment, the cPPT and CTS regions are inserted in the vector in order to a form a flap sequence i.e., a sequence able to adopt a triplex structure after retrotranscription.

It is noteworthy that all the sequences originating from retroviruses or lentiviruses are used as a DNA fragment isolated from its natural (viral genome) nucleotide context i.e., out of the context of the gene or region in which it is naturally contained in the retrovirus or lentivirus genome. Therefore, the sequence is used, in the present invention, deleted from the unnecessary 5' and 3' parts of its natural gene or region, and is recombined with sequences of different origin. These sequences may be either prepared synthetically (chemical synthesis) or by amplification of the lentiviral or retroviral DNA, such as by Polymerase chain reaction (PCR).

The expression "lentivirus" or "lentiviral" denotes a category of retroviruses particularly preferred for the present invention. Examples of lentiviruses include, but are not limited to human lentiviruses such as HIV (in particular HIV-1 or HIV-2), simian immunodeficiency virus (SIV), equine infectious anemia virus (EIAV), feline immunodeficiency virus (FIV), Caprine Arthritis Encephalitis Virus (CAEV) and the VISNA virus.

The genetic material also comprises at least one target polynucleotide, in particular one target polynucleotide, for which variants are desired. The particles containing this target polynucleotide are said "parental", since the target polynucleotide has not undergone yet the mechanisms of genetic variability resulting from both the retrotranscription and particle production following the implementation of the method of the invention. The determination of the "parental" feature of said lentiviral particles or qualification of prepared lentiviral particles as "parental" is performed or decided prior to implementing the method of the invention i.e., it refers to the characteristics, especially to the nucleotide sequence, enabling to recognize the target polynucleotide as the original polynucleotide for which a diversity is sought.

In a particular embodiment, the target polynucleotide found in the genetic material is heterologous to the viral particle i.e., the target polynucleotide is not identical to any gene or coding sequence found in the retrovirus or lentivirus from which the viral particles of the invention is derived. In an embodiment, the target polynucleotide is not of lentiviral or viral origin, and in particular has a bacterial, mammalian (especially human) or synthetic (non natural) origin. The target polynucleotide may correspond to an entire genomic region (for example a gene with its regulatory sequences), to a gene (with introns, if any), a coding sequence (without introns), a non-coding sequence (such as a promoter) or any nucleotide sequence, either natural, synthetic or hybrid, either as a DNA, RNA or cDNA. The target polynucleotide can lead to the synthesis of a functional RNA, or can be functional by itself (as, for instance, being target of binding by a protein) or encodes a protein. Thus, in a particular embodiment, the target polynucleotide encodes a protein that is chosen in the group consisting of (a) a structural protein, (b) a functional protein, such as pro-drug activation proteins, signal transduction proteins or receptor binding proteins, (c) a protein with enzymatic activity, and in particular enzyme with kinase activity such as deoxycytidine kinase, and (d) a secreted protein, in particular interferons such as interferon λ. It is to be understood that the target polynucleotide for directed evolution using this system is not restricted to protein-encoding polynucleotide and can also be constituted by DNA sequences (as recognition sites for protein binding) or sequences that lead to transcription of RNA sequences of interest.

To drive the expression of said target polynucleotide, regulatory expression elements may be operatively linked to said target polynucleotide. In a particular embodiment, the regulatory expression element comprises or is a "promoter" i.e., a regulatory region of DNA generally located upstream of the target polynucleotide (in the 5' region of the sense strand) that generally promotes gene transcription. In other words, it is a specific nucleotide sequence in DNA, flanking the start of the target polynucleotide which instructs an RNA polymerase where to start transcribing RNA. In the present invention, any promoter able to promote the expression of the target polynucleotide in a cell, in particular a mammalian cell (e.g. a human cell) is included within the scope of the present invention. Thus promoter is advantageously an exogenous (non-viral) promoter. Such exogenous non-viral promoter can include, for instance, elongation factor 1-α (EF1-α), CMV, SV40, beta globin and PGK.

In a preferred embodiment, the genetic material also comprises a selectable marker gene, optionally under the control of a secondary regulatory expression element. The expression "selectable marker gene" refers to a gene coding for a protein allowing selection of the cell transduced with the lentiviral particle of the invention. For instance, the gene may code for, but is not limited to, a protein conferring resistance to an antibiotic (e.g. puromycin), a surface protein such as CD69, or a protein encoding a fluorescent marker. The optional secondary regulatory expression element is defined as above for the regulatory expression element linked to the target polynucleotide. However, it is preferable that the two regulatory expression elements (for examples two promoters) be different, although it is clear to one skilled in the art that other methods of expression of the second gene could be also used, as the use of internal ribosome entry sequences (IRES). Promoters which may be used advantageously in accordance with the present invention include for example, EF1-α, CMV, SV40, beta globin and/or PGK.

In a particular embodiment, the genetic material of the invention comprises, in addition to regulatory elements necessary for the transfer, transcription and optionally expression of said genetic material into the genome of a cell, at least one target polynucleotide (in particular one target polynucleotide and/or in particular a heterologous target polynucleotide) under the control of a first promoter (in particular exogenous), at least a second exogenous promoter driving the expression of a selectable marker gene, at least one selectable marker gene (e.g. puromycin-resistance gene). Consequently, and according to a preferred embodiment of the present invention, the genetic material, of the replication-defective lentiviral particles contemplated by the present invention, comprises a 5' LTR, a first promoter driving the expression of a target polynucleotide, a selectable marker gene, a second promoter driving the expression of the selectable marker gene, and a 3' LTR, all of which are defined hereinabove. Examples of such genetic material are illustrated in FIGS. 3A to 3D. It is clear to a person skilled in the art, that the promoter sequences mentioned above can be replaced by other promoters, according to the desired strength of each promoter for the expression of each corresponding target polynucleotide or selectable marker gene. An inducible promoter can also be used, if desired. However it must be understood that the invention is not limited to the use of one target polynucleotide and a selectable marker gene and/or promoters, and less or more such entities can be used.

In a particular embodiment, the target polynucleotide is inserted in such a way that the target polynucleotide is operatively associated with the first promoter (this is not restrictive though, and the polynucleotide target of the evolution experiment could also be constituted by the second target polynucleotide). For instance, the target polynucleotide may be inserted between the first and the second promoters of the genetic material, in particular downstream the first promoter and upstream the second promoter. For instance, such target polynucleotide may code for deoxycytidine kinase (dCK). An example of genetic material (also called vector) is the plasmid SDY-PdCK encoding the dCK gene (FIG. 3D), transduced in XL10 cells deposited at the CNCM (Collection Nationale de Cultures de Microorganismes; Institut Pasteur; Paris, France) under accession number I-3991 on May 14, 2008 (XL10-SDY-PdCK), in the name of Institut Pasteur, 25-28 rue du Docteur Roux, 75724 Paris Cedex 15.

In the present invention, the lentiviral particles used are said replication-defective i.e., once the lentiviral particle has entered into a cell, it cannot replicate alone to form new particles. Thus, the genes encoding the viral proteins necessary for the replication of the virus are not present or are defective, in the lentiviral particles. Typically, such a defect may be due to a mutation and/or deletion of one or more viral structural and replication functions (e.g. the gag, pol and env genes) in the genetic material. In a particular embodiment, the genetic material as described in detail above does not comprise the functional gag gene, the functional pol gene and/or the functional env genes of the lentivirus used as a basis to prepare the transfer vector carrying the genetic material. In a particular embodiment, partial sequences of said genes may be present in the genetic material, such the ψ sequence (element overlapping the gag gene) or the cPPT-CTS region (a fragment derived from the pol gene). In another particular embodiment, the genetic material does not comprise any of the coding genes normally comprised in the lentivirus or retrovirus genome.

Because of their deficiency in replication, the replication-defective lentiviral particles of the invention are obtainable by a transcomplementation system (vector/packaging system). A distinction must be made between step a) to obtain the parental replication-defective lentiviral particles, and step c) to obtain the Fn to Fn+1 replication-defective lentiviral particles.

In order to prepare parental (P) replication-defective retroviral, especially lentiviral particles of step a), permissive cells (such as 293T cells) are transfected in vitro with a plasmid containing the genetic material discussed above, and at least one plasmid providing, in trans, the gag, pol and env sequences encoding the polypeptides Gag, Pol and the envelope protein(s), or for a portion of these polypeptides sufficient to enable formation of retroviral or lentiviral particles. As an example, permissive cells are transfected with a first plasmid comprising the genetic material defined above (transfer vector), a second plasmid (envelope expression plasmid or pseudotyping env plasmid) comprising a gene encoding an envelope protein(s) and a third plasmid (encapsidation plasmid or packaging construct) expressing the Gag and Pol proteins. Processes for the preparation of such particles are disclosed in the literature and are well known from the skilled person. They are also illustrated in the examples.

In contrast, in step c) (detailed below), the genetic material is already integrated in the producer cells (following the transduction of the producer cells with replication-defective lentiviral particles), and therefore the transcomplementation step comprises or consists in transfecting in vitro a previously transduced producer cell with at least one plasmid providing, in trans, the gag, pol and env sequences encoding the polypeptides Gag, Pol and the envelope protein(s), or for a portion of these polypeptides sufficient to enable formation of retroviral or lentiviral particles. As an example, previously transduced producer cells are transfected with a first plasmid (envelope expression plasmid or pseudotyping env plasmid) comprising a gene encoding an envelope protein(s) and a second plasmid (encapsidation plasmid or packaging construct) expressing the Gag and Pol proteins.

In both cases (steps a and c), the replication-defective lentiviral particles of the invention may be pseudotyped with the envelope protein of the lentivirus used to prepare the lentiviral particles, or alternatively with a heterologous envelope protein that is chosen with respect to the cells to be targeted. In a particular embodiment, these envelope proteins are amphotropic (wide host range). In a preferred embodiment, said lentiviral vector is pseudotyped with a VSV-G protein. The VSV-G glycoprotein may originate from different serotypes of vesiculoviruses. In another embodiment, said lentiviral particles are pseudotyped with a protein chosen in the group consisting of the MuLV amphotropic envelope, the Mokola envelope, the EboZ envelope, the Ebola-Reston (EboR) envelope, the influenza-hemagglutinin (HA) envelope, the respiratory syncytial virus (RSV) F and G, the Venezuelan equine encephalitis, the Western equine encephalitis and and rabies virus envelope proteins.

In a second step (step b), the parental replication-defective lentiviral particles as defined above are used for transducing producer cells. Within the present application, the term "transducing", "transduced" or "transduction" refers to the process of introducing the genetic material as described herein into the cytoplasm of a cell, in particular producer cells, following the contact of this cell with the replication-defective lentiviral particles (either parental or the following generated particles such as F1 to Fn+1) with these cells. As explained above, the envelope proteins of the replication-defective lentiviral particles are chosen according to the nature of the cells in which the genetic material has to be integrated. Thus, after recognition by the envelope proteins of the particles of the cell membrane proteins (producer cells or target cells), membranes of the particle and of the cell are fused and the genetic material is transported into the cell cytoplasm. As explained above, the genetic material (under the form of RNA molecule) is reverse transcribed, using the proteins found in the core of the particle, in double stranded DNA that is then imported into the nucleus and integrated into the genome of the cell.

Producer cells that can be used in the present method are well known from the person skilled in the art. When an HIV-based lentiviral system is used, producer cells are of human origin, such as the Human Embryonic Kidney (HEK) 293T cells (ATCC CRL-1573). If other lentiviruses are used, the producer cells can be of mammalian origin in general, depending on the type of lentivirus used.

Optionally, the transduction of producer cells may be carried out in the presence of a mutagen, by exposing producer cells to the mutagen (for example during 48 hours) simultaneously to the transduction of replication-defective lentiviral particles. The mutagens used should preferentially be mild mutagens in order to limit the introduction of mutations that could be deleterious, if too frequent, for the sequences essential for the functionality of the lentiviral vector. Examples of mutagens that may be used are the 5-hydroxy-2'-desoxycytidine (5-OH-dC) (Loeb et al. 1999) or the KP-1212, administered as the prodrug KP-1461 (Anderson et al. 2004, Daifuku et al. 2003 and Harris et al. 2005) (see also "Dangerous Properties of Industrial Materials", 7th Ed., by N. Irving Sax and Richard J. Lewis, and www.evol.nw.ru/~spirov/hazard/mutagen_1st.html). The inventors have demonstrated that using mutagens at this stage increases the rate of mutations by a factor 2-3, and thus reduces the number of transduction steps required to obtain a variability in the sequence of the target polynucleotide. Thus, increasing the mutations rate by 3 times is important particularly for experiments with a scale of duration of 1-2 years range, since it reduces the time required to reach the same complexity of the library to 4-8 months.

Conditions of transduction enabling the lentiviral particles to enter in contact with host cells (producer cells or target cells) and the genetic material to be integrated, are given in the examples and are summarized herein. Supernatant containing replication-defective lentiviral particles as defined above is used to transduce $5 \times 10^6$ fresh HEK 293T cells in a final volume of 5 ml in the presence of 2.5 µl of polybrene. Cells are first incubated 5 hours at 37° C. in 60 mm Petri dishes non-treated for cell culture, and then transferred to 10 cm cell culture dishes and further incubated for 20 hours at 37° C. Other conditions that may be used to transfer cells (producer cells or target cells) are the following:

for transduction experiments on non-dividing cells, Hela cells were seeded in 48 wells plates at 40,000 cells/well in the presence of 8 µM of aphidicolin (Sigma). Cells were transduced with the replication-defective lentiviral particles as defined above, at a concentration ranging from 1 to 100 ng/ml, 24 hours after the aphidicolin block, which was replenished in the medium at the time of transduction;

for dendritic cells (DC) transduction experiments, 500,000 FLT3L-generated-bone marrow-derived DC (FL-DC) were transduced at day 6 of the differentiation, with replication-defective lentiviral particles as defined above at a concentration ranging from 50 to 300 ng/ml. At 2 days post-transduction, FL-DC were harvested and resuspended in PBS with 2% FCS.

In a further step (step c), producer cells that have been transduced with the replication-defective lentiviral particles (parental or F1 to Fn), are then transcomplemented with viral proteins necessary for the production of a new generation of replication-defective lentiviral particles (Fn to Fn+1). As explained above, because of their deficiency in replication, once the genetic material is integrated into the cell host genome, the host cell is lacking the proteins (both enzymatic and structural) enabling the production of new lentiviral particles (i.e., Gag, Pol and Env proteins). In a preferred embodiment, these proteins are provided by transfecting the transduced producer cells with at least one plasmid harbouring an env gene (preferably VSV-G) and gag and pol genes of a retrovirus or lentivirus. In another embodiment, these proteins are provided transfecting the transduced producer cells with a first plasmid harbouring an env gene (preferably VSV-G) (such as the pHCMV-G plasmid) and with a second plasmid harbouring gag and pol genes of a retrovirus or lentivirus (such as the pCMVΔR.2 plasmid). The term "transfecting", "transfected" or "transfection" refers to the introduction of a nucleic acid into a cell, preferably by the intermediary of a plasmid, such as for example by calcium phosphate transfection or using cationic polymers or lipopolyamine (for example polyethyleneimine or PEI).

Following the transcomplementation step, new replication-defective lentiviral particles of the first filial generation of from the Fn to Fn+1 are synthesized and produced in the supernatant of the producer cell culture. In order to carry out new rounds of transduction, these new replication-defective lentiviral particles are collected and separated from producer cells (step d). An example of process for collecting new replication-defective lentiviral particles includes filtration (for example with a 0.45 micron filter) and then concentration using ultrafiltration, such as centrifugal filtration (for example using Vivaspin from Sartorius Stedim biotech).

To ensure that variability is introduced in the sequence of the target polynucleotide, steps b) to d) are repeated consecutively n times, wherein n is 1 or more (step e). By "consecutively" or "consecutive", it is meant that the whole process, consisting of transduction (e1), transcomplementation (e2) and collection of replication-defective lentiviral particles (e3), is repeated n times, each additional process following the end of the previous one. Thus, once a new generation of replication-defective lentiviral particles has been collected, this new generation is transduced in fresh producer cells. By "fresh producer cells", it is meant that these cells have never been transduced yet with lentiviral particles. For example, the replication-defective lentiviral particles obtained after step b) to d) are from the first filial generation (F1). They are used to implement step e) to generate the second generation of replication-defective lentiviral particles (F2). These F2 particles are then used to implement step e) to generate the third generation of replication-defective lentiviral particles (F3), and so on to generate, after implementing n times the whole step e), the n+1 generation of replication-defective lentiviral particles (Fn+1).

Following steps a) to e) of the method, a population (set or mix) of replication-defective lentiviral particles of the n+1 filial generation is obtained, the particles containing indifferently the target polynucleotide or any nucleotide variant of this target polynucleotide. Therefore, the population of particles contains different nucleotide variants of the same target polynucleotide. Indeed, following each transduction step (b and e1), the RNA molecules contained in the replication-defective lentiviral particles is reverse transcribed in double strand DNA before integration into the genome. Since the average error of the reverse transcriptase is about $3 \times 10^{-5}$ per nucleotide, each retrotranscription step leads to one nucleotide error for $3 \times 10^5$ retrotranscribed nucleotides. Moreover, the complexity of the variants of the target polynucleotide may be increased by the recombination carried out between the two RNA molecules contained in the same replication-defective lentiviral particles. These two mechanisms cause the production of variants of the target polynucleotide. By "target polynucleotide", it is meant the polynucleotide inserted in the genetic material used to produce the parental replication-defective lentiviral particles (P) and whose nucleotide sequence is the target for the generation of mutation(s) after implementation of the method of the invention, giving rise to target polynucleotide variants.

The expression "target polynucleotide variant" refers to a nucleotide sequence similar to the sequence of the target polynucleotide i.e., having at least 80%, at least 90%, at least 95% or at least 99% similarity over the whole length with the sequence of the target polynucleotide. Target polynucleotide variants may also be defined by the fact they differ from the sequence of the target polynucleotide by one or more nucleotide substitutions (e.g. 2, 3, 4, 5, 6, 7, 8, 9 or 10), deletion(s) and/or insertion(s). In the embodiment wherein the target polynucleotide encodes a protein, the variants may in some embodiments also be defined by the fact that the one or more nucleotide substitutions (as defined above) leading to amino acid, conservative, semi-conservative or non-conservative, substitution(s) in the resulting protein variants. The expression "protein variant" refers to a sequence similar to the sequence of the protein (the protein encoded by the target polynucleotide) i.e., having at least 80%, at least 90%, at least 95% or at least 99% similarity over the whole length with the sequence of the protein. Variants may also be defined by the fact that they differ from the sequence of the protein by one or more amino acid, conservative, semi-conservative or non-conservative, substitution(s) (e.g. 2, 3, 4, 5, 6, 7, 8, 9 or 10), deletion(s) and/or insertion(s).

To increase the complexity of the target polynucleotide variability, transduced producer cells may be optionally overtransduced with replication-defective lentiviral particles of the same generation as the ones used to transduce the producer cell lines, and obtained from separate cultures of the previous transcomplemented producer cell lines.

Thus, in a particular embodiment of the invention, step e) also comprises before step e2) overtransducing m consecutive times, wherein m is at least 1, the transduced producer cells of step e1) with replication-defective lentiviral particles of the same immediately previous generation as the ones used in step e1), optionally in the presence of a mutagen. In a particular embodiment, the conditions of overtransduction are the same as the conditions used in step e1) for the transduction step. The term "overtransducing", "overtransduced" or "overtransduction" refers to the process of transduction, at least two consecutive times, of transduced producer cells (already transduced by replication-defective lentiviral particles of the same generation) with replication-defective lentiviral particles. In a preferred embodiment, the replication-defective lentiviral particles used for the m consecutive overtransductions (m is at least 1) have been collected from cultures separately transcomplemented (in space) from the producer cells which give rise to the Fn+1 cell generation, the latter being used for overtransduction. Each step e) of the method (repeated n times) is chosen independently from the previous and/or following steps e) of the method. "Chosen independently" means that each time a new generation of replication-defective particles is collected, the method may be implemented either with a step e) with the addition of overtransduction or with a step e) without overtransduction, according to the complexity searched. It is noteworthy that the overtranduction process may be implemented at any Fn generation of particles. An example of overtransduction is described in FIG. 5.

Thus, as an example, the method comprises a first step e) without overtransduction, followed by a second step e) with overtransduction:

e1) transducing fresh producer cells with the immediately previous generation of replication-defective lentiviral particles (Fn−1), optionally in the presence of a mutagen, thereby obtaining the Fn filial cell generation; this step is similar to step e1) disclosed above.

e2) transcomplementing, in parallel, several cultures of transduced producer cells of step e1) with viral proteins necessary for the production of a n generation of replication-defective lentiviral particles (Fn) and obtaining several cultures of producer cells producing a n generation of replication-defective lentiviral particles; "in parallel" means that identical cultures, but separated in space, are transcomplemented as explained before;

e3) collecting, separately, the n generation of replication-defective lentiviral particles (Fn) obtained from the several cultures of transcomplemented cells of step e2);

e4) transducing fresh producer cells with the replication-defective lentiviral particles (Fn) obtained from one of the cultures of step e2), optionally in the presence of a mutagen;

e5) overtransducing m consecutive times the transduced producer cells of step e4) with the replication-defective lentiviral particles obtained from the other several cultures of producer cells of the previous step e2) under the same conditions as step e4), optionally in the presence of a mutagen, wherein m is at least 1; in this step, "consecutive" has the same meaning as above. Replication-defective lentiviral particles obtained from the identical, but separated in space, cultures obtained in step e2) are used to transduce already transduced producer cells (overtransduction). By this way, the genetic material of different particles is integrated in the same cell genome, thus allowing the generation of further diversity through recombination at the next transduction step;

e6) transcomplementing, the last overtransduced producer cells with viral proteins necessary for the production of a n+1 generation of replication-defective lentiviral particles (Fn+1); and e7) collecting the n+1 generation of replication-defective lentiviral particles (Fn+1) from the overtransduced cells of step e6).

The method of the invention may also optionally comprise after each time the producer cells have been transduced for the first time with replication-defective lentiviral particles (i.e, not after over-transduction), a step of selecting the producer cells having integrated in their genome the genetic material contained in the replication-defective lentiviral particles. This selection step may be carried out by any method enabling to determine the correct integration of the genetic material (PCR, detection of LTR). In a particular embodiment, and when the genetic material contains a selectable marker gene, the selection is carried out by detecting the protein encoded by this gene (by ELISA or FACS) or by detecting the effect of this gene (for example resistance to antibiotics). In a particular embodiment, the selectable marker gene is an antibiotic-resistance gene such as the puromycin-resistance gene. It is noteworthy that it may be useful, after each transduction step, to isolate transduced clones of producer cells for sequencing all or part of the heterologous target polynucleotide inserted in the genome of the producer cell of step (d) to analyse the genetic variability generated (variants of the target polynucleotide). In the particular case in which the selectable marker gene is involved in antibiotic resistance, cells that have not been transduced or that have not integrated in their genome, the reverse transcription product of the genetic material will be removed, for example, by treatment with an antibiotic (e.g. puromycin). In addition, the cells containing the selectable marker gene can be stored at any cycle or after n times, providing a stock for restarting the experiment if accidental technical problems are encountered during the subsequent cycles.

The present invention also discloses an in vitro method of generating a cell library expressing genetic diversity variants of a target polynucleotide, comprising:

f) implementing the in vitro method of generating diversity in the nucleotide sequence of a target polynucleotide as described in the present application; and g) transducing target cells with the n+1 generation of replication-defective lentiviral particles, in conditions enabling a cell to be transduced by one of said particles; thereby obtaining a library of target cells comprising cells containing the target polynucleotide or nucleotide variant of the target polynucleotide.

The conditions of transduction enabling the replication-defective lentiviral particles of the Fn+1 generation, to enter in contact with target cells and the genetic material to be integrated into the genome of the target cells, may be the same as the ones disclosed above for the transduction of producer cells. The term "target cell" refer to any cell whose the particular phenotype to study is known i.e., that the behaviour of the target cell regarding a particular function (enzymatic activity, molecule secretion, cell interaction, . . . ) is known. Target cells are used for highlighting the presence of a desired phenotype after transduction with the lentiviral vectors described in the present invention. Target cells might, or might not, be different from the "producer cells" described above. In a particular embodiment, the target cell is a mammalian cell, and in particular a human cell, such as Hela TK- cells, cells lines deleted for SLP-76 or reporter HL116 cells.

In a particular embodiment, the producer cells used in the various steps of the method of the invention are all of the same type and are of the same type as the target cell. In another embodiment, different producer cells are used during the procedure, according to the requirements of the specific experiment. In third embodiment, these producer cells are of a different type with respect to the target cell.

It is noteworthy that the replication-defective nature of the lentiviral vector allows a clonal analysis of the variants of the target polynucleotide, since the absence of any further viral replication, after the $n^{th}$ step of transduction, in the transduced target cells (step g of the method) results in the controlled delivery of only one target polynucleotide variant (optionally encoding a variant protein) in the target cell. Therefore, the cells of the library differ from each other by the fact they contain, integrated into their genome, the target polynucleotide or any variant of the same target polynucleotide, as a result of the variability introduced in the target polynucleotide following the transduction steps and optionally overtransduction steps.

The present invention also relates to a method of screening a variant of a target polynucleotide associated with a cell phenotype comprising:

h) implementing the in vitro method for generating a cell library expressing genetic diversity variants of a target polynucleotide, as defined herein, with step g) of this method being carried out on target cells having an original phenotype;

i) isolating the target cells having a final phenotype that is different from the original phenotype; and j) identifying the variant of the target polynucleotide (or the sequence of the target protein when appropriate) integrated into the cell having said final phenotype, in particular by carrying out the sequencing of the integrated target polynucleotide variant.

By "target cells having an original phenotype" or "original target cells", it is meant a target cell as defined above, in which a phenotype of interest is observed when said cells have not been transduced by the replication-defective lentiviral particles or before their transduction with replication-defective lentiviral particles. A "phenotype" is defined as any observable property of the target cell, which may be put in evidence directly (on the target cell itself) or indirectly (not on the target cell). A phenotype may correspond to a physical, biochemical or physiological trait of the target cell, observable on the cell or following interaction of the cell with its environment. The phenotype of interest is chosen according to the nature of the target polynucleotide inserted in the genetic material in step a) of the method to generate the cell library. Examples of phenotypes are disclosed below:

1) secretion or absence of secretion of a molecule by the target cell;
2) secretion of a functional or a non-functional molecule
3) presence or absence of an activity, for example enzymatic activity, of an intracellular molecule;
4) interaction or absence of interaction of the target cell with secondary cells in culture, for example revealed by the effect of the target cell on the secondary cells. The effect may be any modification of the behaviour of the secondary cells after their contact with the transduced target cell. The expression "secondary cells" means that the phenotype of the transduced target cells is revealed on cells that are put in contact with the transduced target cell; and
5) features defining a particular morphology of the target cell;

"Final phenotype" is defined as the phenotype (as defined above) observed once the genetic material of the replication-defective lentiviral particles has been integrated in the genome of the target cell. Since the only genetic difference between the non-transduced target cells and the transduced target cells is the integration of the retrotranscribed product of the genetic material contained in the replication-defective lentiviral particles, the observed final phenotype results necessarily from the integration of the target polynucleotide (optionally, encoding a protein).

In the method of screening, a particular attention is drawn to any target cell whose final phenotype is different from the original phenotype i.e., to any target cell whose phenotype has changed after the transduction of the replication-defective lentiviral particles. These target cells, for which the phenotype has changed after transduction, are isolated by any means known to the person skilled in the art, and with respect to the difference of phenotype.

Figure 7:
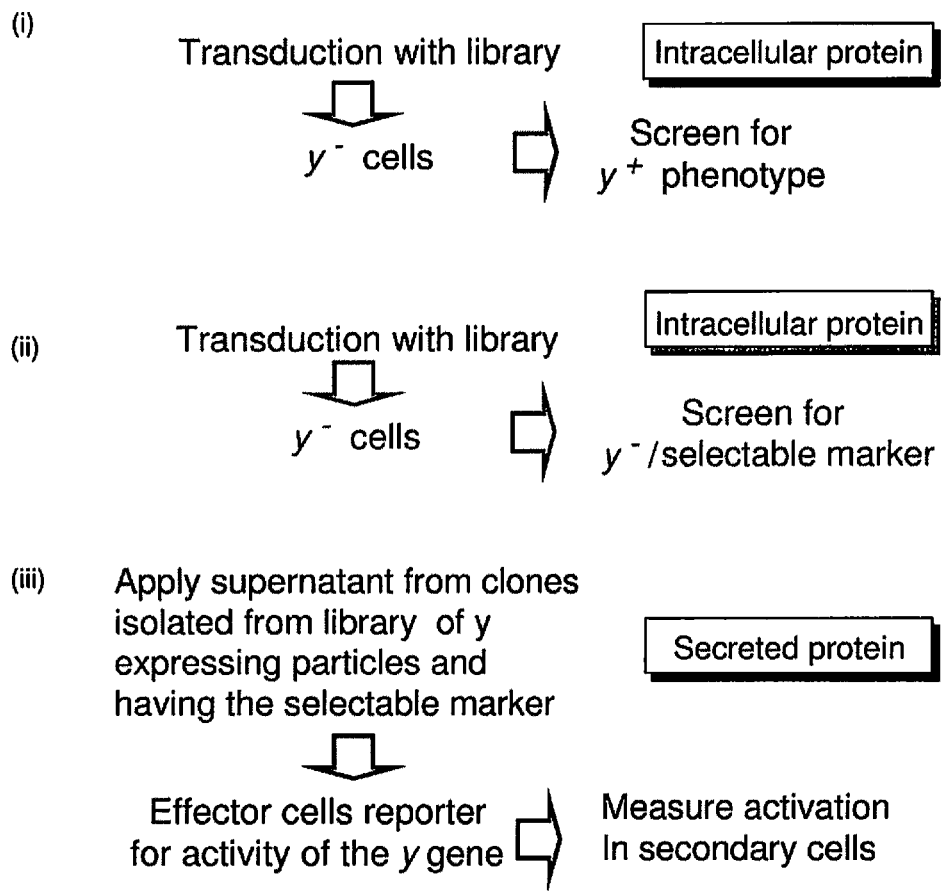
FIG. 7 is a diagram illustrating three (3) types of selection steps conducted within the method of the present invention.

As examples and referring to the four (1 to 5) examples of phenotype described above, the following Table 1 lists the difference of phenotype that can be observed and the means to detect this difference.

secreted protein, selection may occur by positive selection on secondary cells (FIG. 7). A target polynucleotide is considered to be associated with the expression of a protein, when modification in this target polynucleotide influences (e.g. inhibits, decreases or increases) the expression of this protein, though the coding sequence of this protein is not modified or altered. This can be the case, for example, of transcription or expression regulatory elements, such as promoter, enhancer, . . .

TABLE 1

Examples of phenotype that can be observed on transduced target cells and examples of means to detect a difference in the phenotype after transduction;

| Example | Original phenotype | Final phenotype | Examples of mean of detection of the phenotype |
|---|---|---|---|
| 1) | Secretion of a molecule<br>Absence of secretion of a molecule<br>Absence of secretion of a molecule | Absence of secretion of a molecule$^b$<br>Secretion of a Molecule$^a$<br>Absence of secretion of a molecule$^c$ | ELISA, cytometry |
| 2) | Secretion of a functional molecule<br>Secretion of a non-functional molecule | Secretion of a non-functional molecule<br>Secretion of a functional molecule | Detection of the molecule and/or assay of its functionality |
| 3) | Activity of an intracellular molecule<br>Absence of activity of a intracellular molecule<br>Absence of activity of a intracellular molecule | Absence of activity of a intracellular molecule$^b$<br>Activity of an intracellular molecule$^a$<br>Absence of activity of a intracellular molecule$^c$ | Growth of target cells on a medium requiring the activity (otherwise, cell death) |
| 4) | Particular effect of the target cells on secondary cells in culture<br>Absence of effect of the target cells on secondary cells, in culture | Absence of effect of the target cells on secondary cells<br><br>Particular effect of the target cells on secondary cells | Identification of a modification of the effect of the target cell on the secondary cells (e.g. morphology of the secondary cell, differentiation of the secondary cell, secretion of molecule by the secondary cell, death of the secondary cell) |
| 5) | A particular cell morphology | Different morphology | fluorescence, microscopy |

$^a$positive selection on a negative genetic background,
$^b$negative selection on a positive genetic background,
$^c$negative selection on a negative genetic background.

Once a difference of phenotype has been put in evidence (comparison of the phenotype of the target cell before transduction and after transduction), this target cell is isolated. The term "isolated" or "isolating" means, when referring to the phenotype of a target cell, that the target cell has a separate and discrete final phenotype with respect to the other target cells of the culture or library. The isolation of the target cells with the final phenotype can be performed by any method known to a person skilled in the art. Of course, depending on the nature of the target polynucleotide (in its original or variant version) comprised in the lentiviral particles, different isolation or selection methods may be used to select the target cells that have incorporated in their genome the genetic material encoding the target polynucleotide variant which is associated with the desired phenotype.

For instance, if the target polynucleotide is associated with the expression of an intracellular protein (or encodes said intracellular protein), the isolation step of the present invention may occur by (i) positive selection on a negative genetic background, by (ii) negative selection on a negative genetic background, or by (iii) negative selection on a positive genetic background. If, however, the target polynucleotide is associated with the expression of or encodes a Positive selection on a negative genetic background (i) can be performed by transduction of target cells (preferably human target cells) that do not exhibit the activity or do not express the desired molecule and selection for those target cells that have acquired the desired activity or express the desired molecule. In other words, the isolation step comprises isolating target cells having a desired activity or expressing a desired molecule, whereas the original target cells before transduction in step g) respectively lack the desired activity or do not express the desired molecule For performing a negative selection on a negative genetic background (ii), the transduction of target cells that do not exhibit the activity or do not express the desired molecule is performed. Selection for the transduced target cells that have incorporated in their genome the target polynucleotide and that do not express the activity or do not express the desired molecule may then occur. As such, the selection of target cells that comprise the selectable marker gene, but do not exhibit the desired phenotype is involved. Of note, the presence of the additional selectable marker gene (as resistance to an antibiotic, therefore not linked to the phenotype desired) is essential for this type of selection. In other words, the isolation step comprises isolating the target cells transduced as in step g) that (1) have stably integrated the reverse transcription product generated by the lentiviral vector and (2) have not acquired the desired activity or do not express a desired molecule, as instead would have been found if the transgene carried by the vector encoded a functional product.

A variant of the screening based on negative selection is constituted by performing negative selection on a positive genetic background. By this means one can identify dominant negative mutants, which confer a negative phenotype to originally positive cells. As a particular embodiment of this option, the isolation step comprises isolating the target cells which, once put in contact with secondary cells, are able to activate or inhibit the activity of these secondary cells or the expression of molecules by these secondary cells (for example by activating the production of a fluorescence reporter molecule). As an example, by performing a positive selection for a secreted molecule, a variant of the target polynucleotide is targeted. In this type of selection, the supernatant from the clones isolated on the basis of the expression of the selectable marker, is applied to secondary cells in order to assess the activation of a reporter gene in the secondary cells due to the action of the secreted molecule whose expression is associated with or which is encoded by the variant of the target polynucleotide.

In a final step, once the target cells are isolated, the variant is identified by any means enabling to distinguish it from the target polynucleotide, ideally through the phenotype of the target cell. If not possible, other approaches could be followed as, for example by restriction fragment length polymorphism (RFLP) or on arrays. When the target polynucleotide encodes a protein, the variation may also be identified on the encoded protein, for example by measuring the isoelectric point or measuring the size on polyacrylamide gel. In particular embodiment, the target polynucleotide is sequenced and the variation at the level of the nucleotide sequence and optionally at the level of the protein sequence is determined. The sequencing is advantageously carried out by amplifying (for example by PCR) the sequence of the target polynucleotide, since the sequences surrounding the target polynucleotide (in 5' and in 3') are perfectly known and thus primers for amplification may be easily designed (see for example FIG. 3D).

Of course, all the variants (nucleotide or protein), the genetic material, the lentiviral vectors and particles described in this application are part as such of the invention.

The present invention also relates to a cell library, preferably a mammalian cell library, in particular a human cell library, comprising cells having integrated in their genome a target polynucleotide or a nucleotide variant of said target polynucleotide, wherein said cell library is obtained following the transduction by a population of replication-defective lentiviral particles of a generation from F4 to F20, preferably F8 to F16, or of at least the $8^{th}$, $10^{th}$, $12^{th}$ or $15^{th}$ generation, these replication-defective lentiviral particles being obtained previously in the absence or presence of a mutagen.

The term "genome" refers to any nucleic acid molecule that is stably present in the target cell, in particular whose presence into the cell is not dependent upon pressure selection. The term "genome" does not encompass plasmids. Primarily, the term "genome" refers to nucleic acid molecules present in the cell nucleus (nuclear genome), by opposition to nucleic acid molecules present in the cytoplasm, and encompasses for example chromosomes. In particular embodiment, the term "genome" also includes nucleic acid molecules present in particular cell compartments, such as organelles, for example mitochondria (mitochondrial genome) or chloroplasts (chloroplast genome).

All the cells or most of the cells in the library differ from each others in the sequence of the integrated target polynucleotide or variant of this same target polynucleotide, as a result of the variability introduced in the target polynucleotide following the transduction steps and optionally overtransduction steps. Indeed, the replication-defective lentiviral particles used for the transduction of the target cells differ in the sequence of the target polynucleotide. The expression "replication-defective lentiviral particles of the at least $8^{th}$ generation" means replication defective lentiviral particles (as defined above) obtained after implementing the method, of generating genetic diversity in the nucleotide sequence of a target polynucleotide, of the invention, wherein n is at least 7; in a particular embodiment, the method is implemented with at least m steps of overtransdcution as defined above.

Thus, most of the cells of the library have integrated in their genome a retrotranscribed target polynucleotide or retrotranscribed target polynucleotide having a sequence different from the original sequence (target polynucleotide variant). All cells of the library are characterized by the fact that they have integrated into their genome the genetic material as defined above i.e., at least the regulatory elements necessary for integration (for example the LTR), the target polynucleotide or the target polynucleotide variant (optionally encoding a protein or its variant) under the control of regulatory expression elements. When the genetic material also contains a selectable marker gene, this selectable marker gene may be used to isolate the cells of the library that have effectively integrated the genetic material into their genome. These elements may be used to characterize the cells of the library. For instance, such a cell library is the library 293T-F8dCK deposited at that CNCM under accession number 1-3992 on May 14, 2008, in the name of Institut Pasteur, 25-28 rue du Docteur Roux, 75724 Paris Cedex 15. This cell library is a population of HEK-293 T cells corresponding to the $8^{th}$ generation obtained by the method of the invention, and containing integrated in its genome the dCK gene or variant thereof, as the target polynucleotide. This cell population may be cultivated in Dubelcco-Modified Eagle's Medium supplemented with 10% fetal calf serum, 100 U/ml penicillin, 0.1 mg/ml streptomycin and 0.6 µg/ml puromycin, at a temperature of 37° C., in 5% $CO_2$.

The present invention also relates to a nucleic acid comprising or consisting in an U3 region of a HIV-1 LTR mutated in positions 24, 82, 108, 160, 164, 183, 198, 251, 291, 333, 421 and 447 with respect to the U3 region of a wild type LTR of HIV-1 virus. In a particular embodiment, the mutated U3 region is characterized by the mutations 24A>C, 82A>G, 108G>A, 160C>A, 164T>G, 183A>G, 198A>C, 251G>A, 291G>A, 333T>C, 421C>G and 447C>T with respect to the U3 region of a wild type LTR of HIV-1 virus, in particular with respect to SEQ ID NO: 5. In a further embodiment, the mutated U3 region has the sequence as defined in SEQ ID NO: 6. The U3 region may be obtained following the implementation of the claimed method in human cells, synthesized chemically or obtained by directed mutagenesis of a wild type U3 region. This mutated U3 region confers an advantage, in human cells, in particular in HEK 293T cells, for the expression of a target polynucleotide from the LTR or from the genetic material as described herein, and is used for this optimized expression. This mutated U3 region is hypothesized to favour ectopic expression in human cells of the target polynucleotide by expressing higher content of genomic RNA (RNA transcribed from the genetic material which has been inserted into the cell genome) than the wild type U3 region.

The invention also concerns a nucleic acid comprising or consisting in a LTR, in particular a HIV-1 LTR, in which its U3 region is mutated in the positions described above or has the mutations as defined above or has a sequence as defined in SEQ ID NO:6. The invention is also directed to the genetic material as defined herein, a lentiviral vector as defined herein comprising this genetic material or a particle as defined herein comprising this genetic material, in which the U3 region of its LTR 5' and/or LTR 3', preferably the LTR3', is mutated in the positions described above or has the mutations as defined above or has a sequence as defined in SEQ ID NO:6. The invention also concerns any lentiviral vector, i.e., a vector derived from a lentivirus, in particular a HIV vector or a HIV-1 vector, in which the U3 region of its LTR 5' and/or LTR 3', preferably the LTR3', is mutated in the positions described above or has the mutations as defined above or has a sequence as defined in SEQ ID NO:6. Is also part of the invention, a cell, a cell culture or a cell library, comprising inserted in its genome a genetic material in which the U3 region of its LTR 5' and/or LTR3' is mutated in the positions described above or has the mutations as defined above or has a sequence as defined in SEQ ID NO:6.

Finally, the invention also relates to the use, in particular in vitro or in cell culture, of replication-defective lentiviral particles comprising a genetic material encapsidated in said particles, wherein said genetic material comprises the regulatory elements necessary for the transfer, transcription and optionally expression of said genetic material in the genome of a cell host and at least one target polynucleotide, for generating diversity in the nucleotide sequence of said target polynucleotide and/or for generating a cell library expressing genetic diversity variants of said target polynucleotide. All definitions and features disclosed above apply to the use of the replication-defective lentiviral particles.

Overall, the main advantage of the method of the present invention is that a library of variants of the target polynucleotide is generated directed in the biological vector (lentiviral particles) that is used to deliver efficiently and in a controlled manner the target polynucleotide to the target cell (in particular the human cell). As such, a crucial feature of the invention is the use of replication-defective lentiviral particles that can be brought back to controlled replication competence, by a transcomplementation system. The replication-defective nature of these particles allows clonal screening for the desired phenotype in the target cells. A further advantage of the method contemplated by the present invention is the use of retroviral recombination, through a procedure that favours it, named overtransduction, to amplify the genetic complexity of the library.

The present invention offers many other advantages as well:

(1) an advantage of retroviral or lentiviral transduction of cells (with particles) with respect to transfection (directly with nucleic acids) is that, by modulating the multiplicity of transduction steps, one can limit the introduction of the target polynucleotide (original sequence or a sequence variant) to not more than one copy per target cell. This is a prerequisite to perform clonal analysis based on the phenotype conferred to the target cell by a single target polynucleotide.

(2) with respect to the use of replication-competent vectors, the use of replication-defective (retroviral or lentiviral) particles for delivering the target polynucleotide allows to rescue, in the transduced target cell presenting the desired phenotype, the target polynucleotide variant responsible for that phenotype. If a virus were used (as in reference Das et al.) the virus would continue to replicate during selection for the desired phenotype and reinfect the target cells in culture with other variants of the target polynucleotide generated in the meantime. This would hamper clonal expansion. Selection for the phenotype conferred by a single target polynucleotide variant would not be possible as neither would be the identification of the target polynucleotide variant responsible for that given phenotype.

(3) with respect to the use of replication-competent viruses, the use of replication-defective (retroviral or lentiviral) particles for delivering the target polynucleotide does not induce any cytopathic effect.

(4) with respect to the use of replication-competent viruses, the use of replication-defective (retroviral or lentiviral) particles for delivering the target polynucleotide allows to pseudotype the viral particles with an amphotropic envelope (as that of the Vescicular Stomatitis Virus; VSV), allowing transduction of a wide range of cells.

(5) using lentiviral-based particles, namely those comprising cPPT-CTS sequences, the library can be used to transduce (and therefore screen for the desired phenotype) also primary and non-replicative (or non-dividing) cells.

(6) the method of the present invention allows direct screening of the desired phenotype in target cells (eukaryotic, mammalian or human cells). More physiologically relevant observations with respect to screening in simpler systems, such as binding in vitro of purified proteins or bacterial genetic screening can thus be obtained with the method of the present invention.

(7) another advantage of the present invention is the fact that target polynucleotide variants that are toxic for the target cells will automatically be excluded during the evolution procedure. In fact, their isolation will likely not occur since, during the procedure of generation of genetic diversity, the target polynucleotide is repeatedly introduced in the cells (through transduction in producer cells) where it is expressed. If toxic, these cells would be eliminated from the culture.

(8) since genomic regions in the 2 to 4 kb range can be targeted in the target cells, the method described herein presents a substantial potential for finding long-range effects of mutations, or for studying large multifunctional proteins.

Thus, the methods of the invention lie on the genetic diversity generated by the two following mechanisms.

Figure 4A:
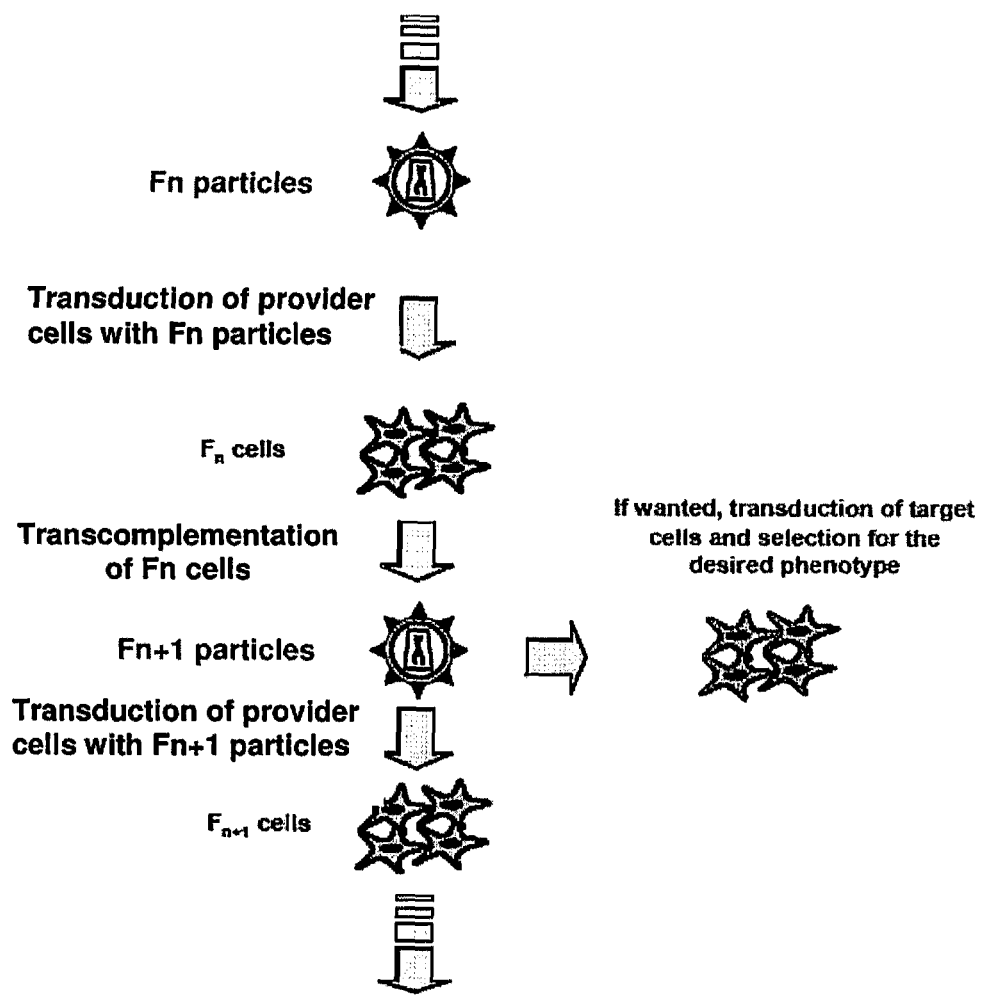
FIG. 4 is a schematic diagram illustrating the procedure followed to produce two subsequent viral generations (Fn and Fn+1) (A). In a preferred embodiment, a selection step is applied, herein with treatment with puromycin (though any selectable marker may be used) (B). The optional selection of target cells possessing the desired phenotype is also indicated.
Figure 4B:
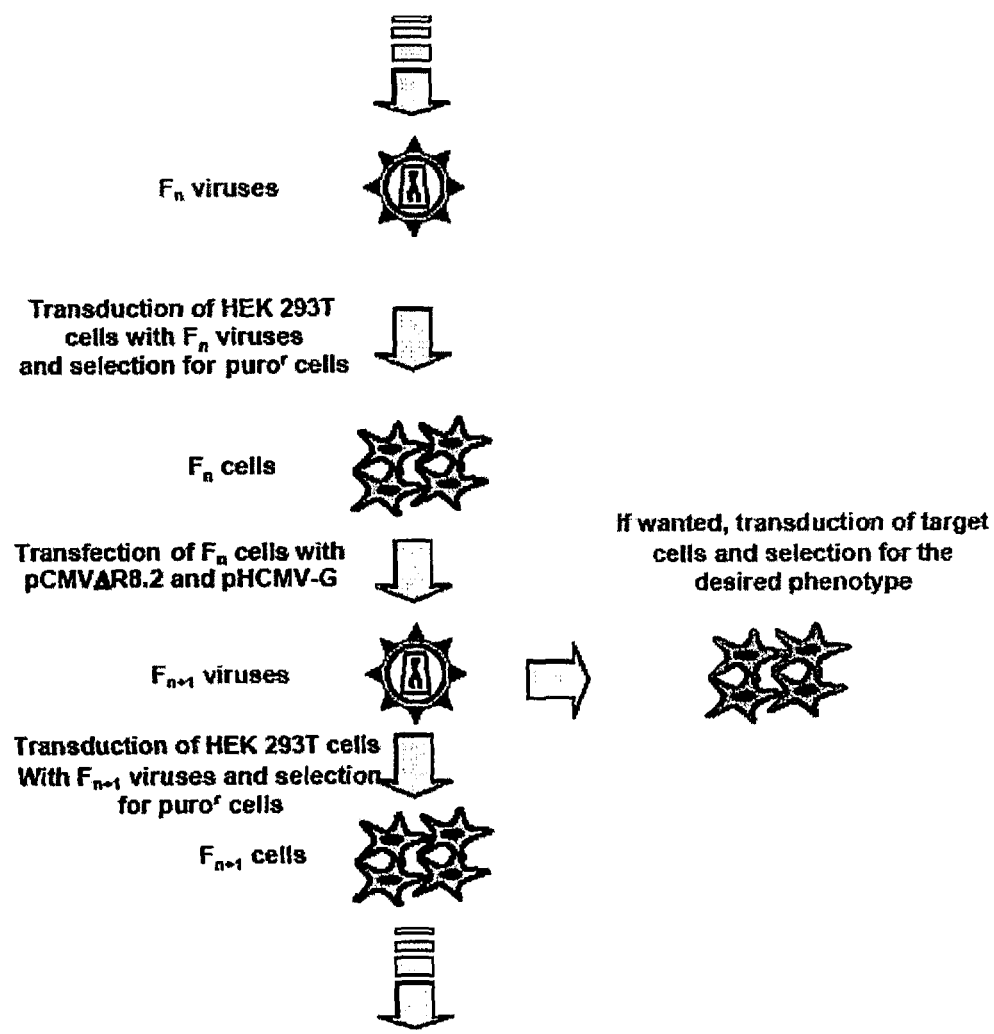

Mutations:

As shown in the example given in FIGS. 4A and 4B, the Fn+1 viral particles (generated by transfecting the cells of the Fn generation) are collected and used to transduce producer cells (for instance HEK 293T cells) that are then selected for their resistance conferred by the resistance marker gene. When overtransduction is performed, the procedure followed is the one outlined in FIGS. 5A and 5B. As the number of generations progresses, the target polynucleotide will evolve by accumulating modifications and recombination events during reverse transcription.

It is known that the average error rate of HIV-1 reverse transcriptase is of $3 \times 10^{-5}$ per nucleotide (Mansky L. M., (1998) J. Gen. Virol., 79 (Pt 6): 1337-45). In control experiments, approximately $2 \times 10^7$ functional viral particles were produced, as judged by the amount of puromycin resistant clones. Consequently, for a 500 nucleotide long target polynucleotide for example, approximately $3 \times 10^5$ mutants will be generated after a single cycle ($3\times10^{-5}\times500\times2\times10^7$). The complexity of the library (i.e., the number of variants of the target polynucleotide) will then increase with the number of transduction and transcomplementation cycles or with every Fn+1 generation. Furthermore, in addition to the introduction of base substitutions, reverse transcription is also responsible for the generation of other important genomic rearrangements, among which the most frequent is recombination.

Figure 5A:
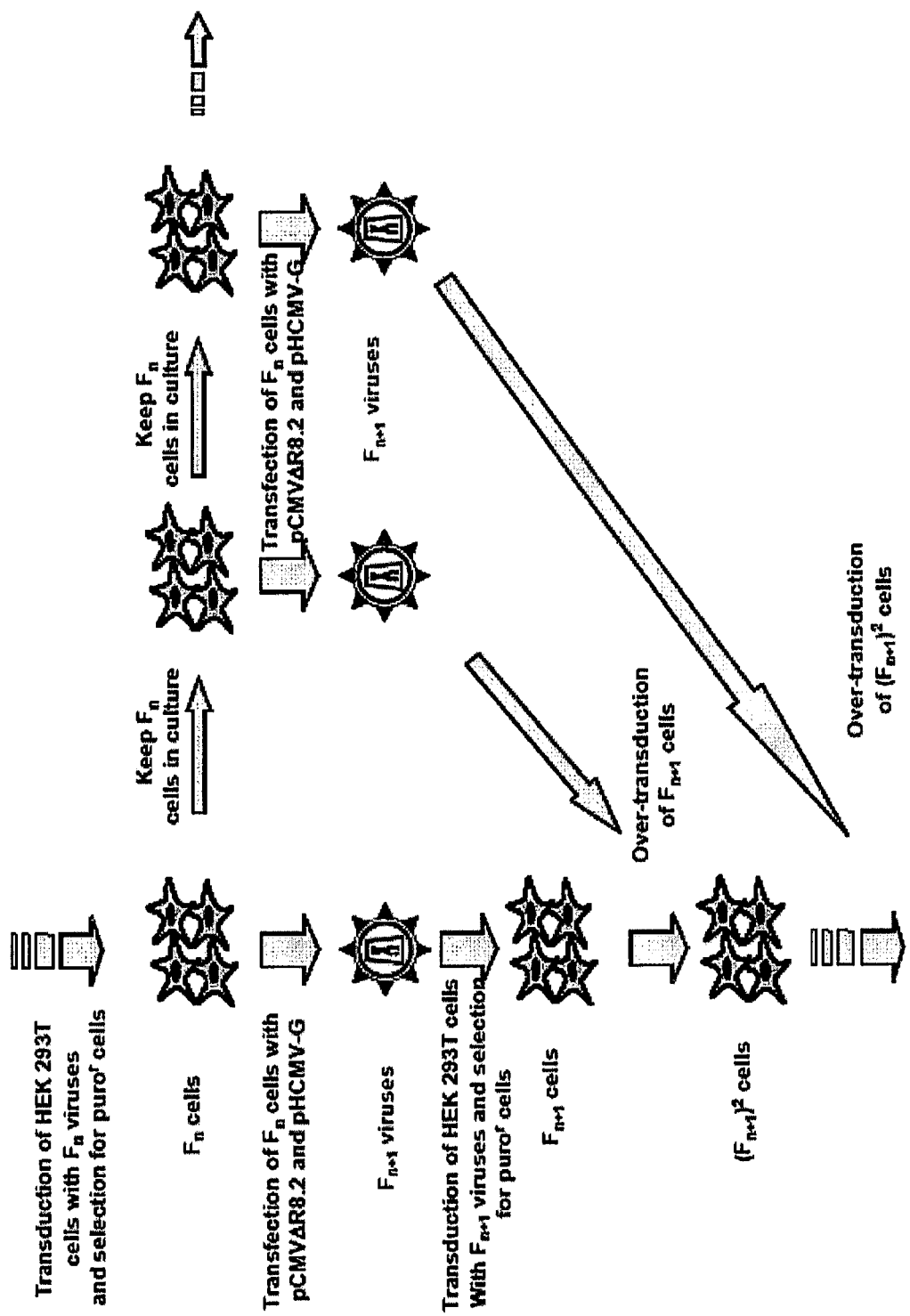
FIG. 5 is a schematic diagram illustrating the overtransduction step that can be implemented within the method of the present invention. The below schematic diagram represent the overtransduction step, and shows two overtransductions (A) in the general procedure and (B) in an specific example where the overtransduction step is used to implement at the $6^{th}$ (F6) generation of the evolution of the dCK gene.
Figure 5B:
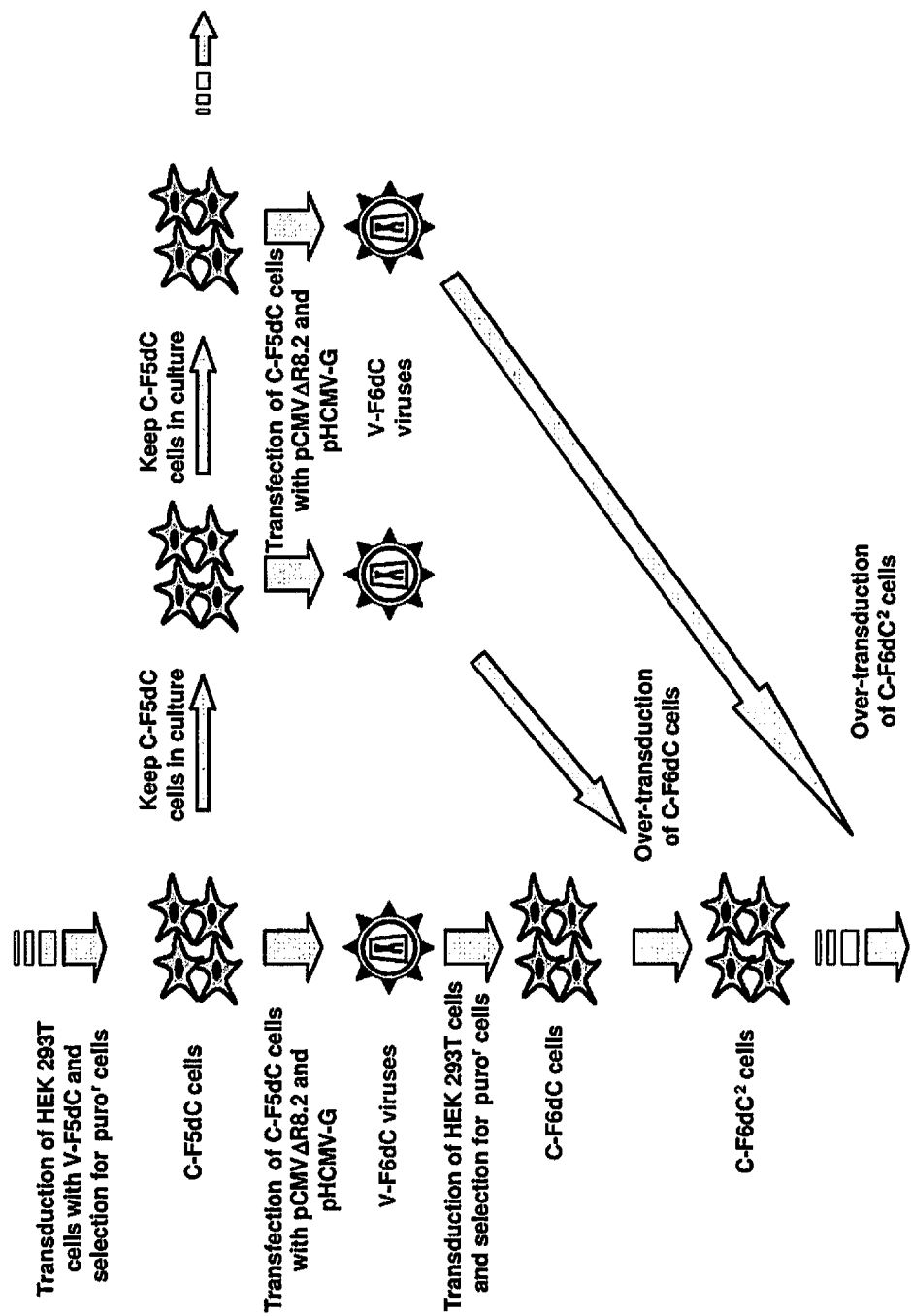

Recombination:

Another immediate advantage of a particular embodiment of the method of the present invention is the overtransduction step, described in the present application. Indeed, to ensure the presence of multiple copies of genetic material in the same producer cell, the method of the present invention is based on multiple successive overtransduction steps (FIGS. 5A and 5B). As such, once a cell population is established (e.g. the Fn population), cells are transcomplemented with helper plasmids to generate the next generation of replication-defective particles (Fn+1) which will be then used to transduce freshly producer cells and optionally to select the transduced producer cells (for example with antibiotics such as the puromycin to select Fn+1 resistant cell population). In the meantime, the Fn cell population may be maintained in culture and used to produce further Fn+1 replication-defective particles which may then be used to transduce previously-transduced Fn+1 cells (overtransduction step). Overtransduction can be reiterated, in principle without limits in the number of times.

Thus, inserting several individual target polynucleotides (for example encoding different versions of the protein) within the same cell will lead to the generation of heterozygous lentiviral particles (i.e., lentiviral particles harbouring two different molecules of genetic material) that, upon transduction of a new cell, can undergo recombination, thereby amplifying genetic variability, as it occurs during natural HIV infection. By reshuffling different regions of the genome, recombination brings about several point modifications in the same genetic background in a single infectious cycle, increasing the repertoire of genetic combinations explored. Recombination occurs during reverse transcription as a consequence of template switching by the reverse transcriptase between the two copies of genomic RNA (herein defined as genetic material) present in the viral particle, a process known to a person skilled in the art as "copy choice". Copy choice occurs at rates of approximately $10^{-4}$ events per nucleotide and per infectious cycle when considering similar sequences.

In the present invention, recombination is expected to increase the complexity of variants at two levels.

At the first level, there is an increase of the sequence space explored by the procedure by reshuffling point mutations introduced during reverse transcription. At the second level, there is the possibility of using related genes as target polynucleotides in the genetic material. If two or more related genes, possessing identical or similar properties are available, related genes can be used simultaneously. Thus, in this option, the parental replication-defective lentiviral particles (P) are generated, in step a) of the method, in permissive cells using, besides the encapsidation plasmid and the envelope expression plasmid, a transfer vector containing the at least two related genes as target polynucleotides or at least two transfer vectors, each containing one related gene as target polynucleotide. Since the RNAs obtained following the transcription of the integrated genetic material possess the same dimerization signal, dimerization of the at least two related RNAs (each from the related target polynucleotide) occurs on a stochastic basis, leading to the generation of heterozygous replication-defective lentiviral particles that carry one copy of each related target polynucleotide. Recombination between these two related target polynucleotides can then occur during reverse transcription. Since recombination displays a clear preference for regions bearing a higher similarity between the two RNAs (Baird H. A., Galetto R., Gao Y., Simon-Loriere E., Abreha M., Archer J., Fan J., Robertson D. L., Arts E. J., and Negroni M., (2006) Nucleic Acids Research, 34, 5203-5216), it is supposed to occur more frequently in the most conserved parts of the gene or in the most conserved coding regions. In particular, when the target polynucleotides encodes proteins, this phenomenon is expected to result in a higher probability of generating functional proteins since the junctions between the two protein sequences is expected to be "smoother" than in cases where the junction involves highly discordant regions. The use of related genes thus constitutes a remarkable potential of this system.

Another application of the invention is that overtransduction by replication-defective lentiviral particles containing in their genetic material selectable marker gene(s) different from the one carried for the transduction step (and also possibly containing in its genetic material a different version of the target polynucleotide from the one carried for the transduction step) can be followed by double selection to selectively isolate the population of cells that have been both transduced and then overtransduced by the two types of replication-defective lentiviral particles. This would allow the evolution of two or more target polynucleotides simultaneously. The evolving target polynucleotides could be genes belonging to the same family of genes, or can be related genes (as for instance desoxyribonucleoside kinases, as indicated in the specific examples provided herein). Interestingly, in this case, recombination can also lead to the generation of chimeric genes between these target polynucleotides.

The objects and other advantages of the present invention will become more apparent upon reading of the following non-restrictive description of preferred embodiments thereof, given for the purpose of exemplification only, with reference to the accompanying drawings.

EXAMPLE 1

Genetic Variability Generated in the dCK Gene

Materials and Methods

Plasmids: The SDY-PdCK plasmid was constructed in the laboratory and the map is provided in FIG. 3D. pCMVΔR8.2 (Naldini L., Blomer U., Gallay P., Ory D., Mulligan R., Gage F. H., Verma I. M. and Trono D. (1996) Science, 272, 263-267) is a plasmid encoding HIV-1 Gag, Pol, and accessory proteins, and pHCMV-G (Yee J. K., Miyanohara A., LaPorte P., Bouic K., Burns J. C. and Friedmann T. (1994) P.N.A.S., 91, 9564-9568) encodes the VSV envelope protein.

Cells: HEK 293T cells are grown in Dulbecco's modified Eagle's medium supplemented with 10% fetal calf serum, penicillin and streptomycin (Invitrogen), and maintained at 37° C. with 5% $CO_2$.

Nomenclature of Cell Lines and Viral Generations

Each viral generation is named V-FXdC, where "V" stands for virus (replication-defective lentiviral particles), "FX" for the generation ("FP" stands for parental viral generation; "F3" stands for third viral generation) and "dC" indicates that the target polynucleotide for the evolution is the dCK gene. Nucleotide sequence of the dCK gene and its corresponding protein sequence are disclosed in SEQ ID NO:1 and SEQ ID NO:2 respectively. For cells, the same procedure is followed replacing V by C, for cells. Therefore, as an example, C-F3dC cells generate V-F4dC particles that, once used to transduce HEK 293T cells, generate the C-F4dC cell line.

Generation of the Parental Cell Line

Genetic diversification of the target polynucleotide begins with the treatment of the cell with calcium phosphate which precipitates and helps the complexed DNA to enter the cell. The generation of parental replication-defective particles by transfection of HEK 293T cells using a mix containing pSDY-dCK (transfer vector), pCMVARΔ8.2 (encapsidation plasmid), and pHCMV-G (envelope expression plasmid) at a weight ratio of 2:2:1 then ensues. Culture supernatant from eight 10 cm plates is collected 48 h after transfection, filtered on 0.45 micron filters, and concentrated using Vivaspin Ultrafiltration Concentrators (molecular weight cut-off 50,000 Da). Concentrated supernatant is then used to transduce $5 \times 10^6$ fresh HEK 293T cells in a final volume of 5 ml in the presence of 2.5 µl of polybrene. Cells are first incubated 5 hours at 37° C. in 60 mm Petri dishes non-treated for cell culture, and then transferred to 10 cm dish culture dishes and further incubated for 20 hours at 37° C. The cells are then detached by trypsin-EDTA treatment and re-seeded in the presence of 0.6 µg/ml puromycin. Once the puromycin-resistant population selected (C-FPdC) the cells are used to continue the experiment and be re-infected.

Generation of the Filial Cell Lines by Transduction

C-FPdC cells are then transfected with pCMVAR8.2, and pHCMV-G at a weight ratio of 2:1, and treated as described in the previous paragraph up to the transduction of fresh HEK 293T cells and the establishment of the next cell generation (C-F1dC) through puromycin selection. The procedure is then repeated generating the C-F2dC cell line, and the subsequent generations up to the F5 cell line (C-F5dC).

Generation of the Filial Cell Lines by Overtransduction

C-F5dC cells are transfected as described above for the generation of particles (V-F6dC). V-F6dC particles, treated as described above, are used to generate C-F6dC cells. In parallel, C-F5dC cells are maintained in culture and used to generate new V-F6dC particles that are used for transduction, once established by puromycin selection, the C-F6dC cell line. This is what we define the overtransduction procedure as shown in FIG. 5B. This generates the C-F6dC2 cell line. Over-transduction with V-F6dC is then done on C-F6dC2 cells, generating the C-F6dC3 cell line. In total, the procedure is repeated four (4) times to generate the C-F6dC5 cell line. During the whole overtransduction procedure, cells are cultured in the presence of puromycin. Finally the C-F6dC5 cell line is used to generate the new generation of particles (V-F7dC). The whole procedure can be repeated, to generate the following generations of particles.

Testing Genetic Complexity for V-F8dC

Figure 1:
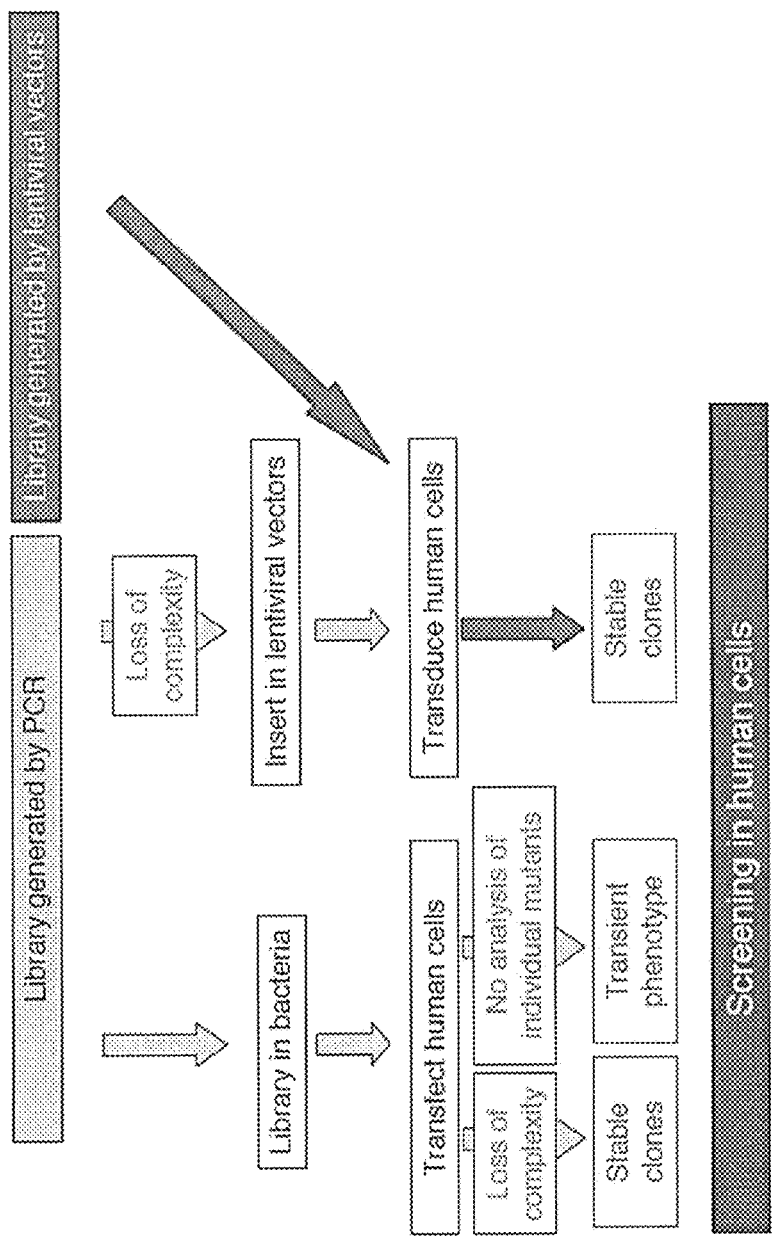
FIG. 1 is a schematic diagram outlining the advantages of the present invention over pre-existing methods to generate diversity in cells (for example mammalian or human cells).
Figure 2:
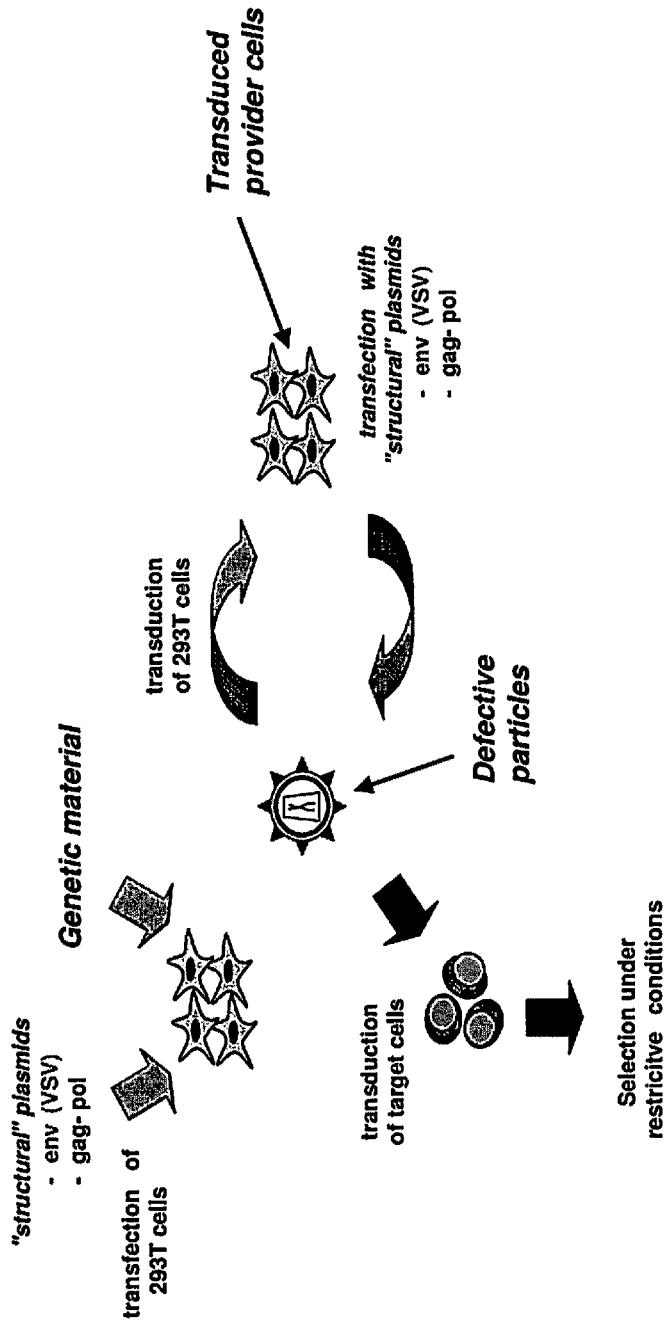
FIG. 2 is a schematic diagram of the different steps of the method of the present invention.
Figure 3:
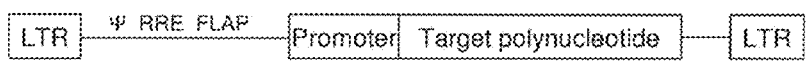
FIG. 3 is schematic diagram of the general structure of the genomic RNAs (genetic material) used in the method of the present invention. The first schematic diagram represents a genetic material with a promoter and the target polynucleotide (A). The second schematic diagram represents a genetic material with a first promoter driving the expression of the target polynucleotide, and a selectable marker gene (marker) under the control of a second promoter (B). The third schematic diagram represents a preferred embodiment of the genetic material, wherein the first promoter is EF1α, the second promoter is human (h) PGK and the selectable marker gene is the puromycin gene. ψ: psi sequence; RRE: Rev responsive element; PPT: polypurine tract; FLAP: cPPT-CTS triplex region (C). The last schematic diagram represents the general structure of another preferred embodiment of genetic material; arrows noted "EF1-CR" and "PGK-CR" are primers designed to amplify the sequence of the target polynucleotide (D)
Figure 3:
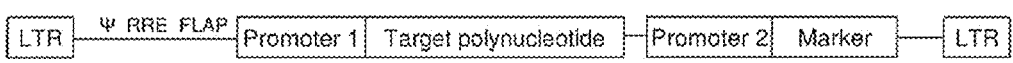
Figure 3:
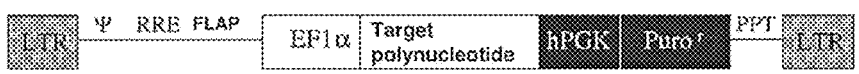
Figure 3:
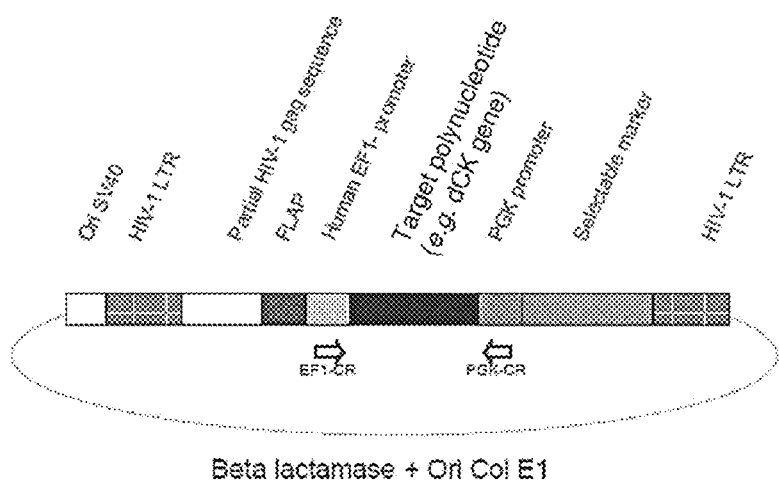

Viral preparation from V-F8dC has been diluted 1:10,000 and used for transduction of $3.5 \times 10^6$ HEK 293T cells as described above. Five hours post-transduction, 1.5 ml of transduced cells are diluted to a final volume of 25 ml and seeded in 96-well plates (100 µl/well). Twenty-four hours later, puromycin is added to a final concentration of 0.6 µg/ml. Single puromycin-resistant clones are then isolated, expanded, and genomic DNA extracted for sequencing of the dCK gene. For sequencing, the cell pellet from a 10 cm plate is resuspended in 250 µl of lysis reagent (Viagen Biotech, Los Angeles, Calif., USA) with 1 µg/ml of proteinase K and incubated overnight at 55° C. The cell lysate is then incubated for 1 hour at 86° C. and 1 µl used as template for PCR amplification with primers PGK-CR and EF1-CR that anneal on the PGK and EF1-α promoters, respectively, as indicated in FIG. 3D. PCR products are then sequenced.

Analysis of the Genetic Diversity Generated in the dCK Gene

Experiments have been conducted on the deoxycytidine kinase (dCK) as the target polynucleotide. The F17 generation has been reached. Clones have been analyzed by sequencing at the F8 generation (cells from this generation have been deposited at the CNCM under accession number 1-3992 on May 14, 2008) and F16 generation. For analysis of the genetic complexity generated by the method of the present invention, HEK 293T cells were transduced, at a low multiplicity of transduction, with the indicated viral generation and were seeded in ten 96-well plates, in the presence of puromycin. Less than 7 wells per 96-well dish resulted to harbor cell proliferation after 10 days, indicating the clonal expansion of an individual puromycin-resistant cell in that well at the time of seeding. Individual clones were expanded, the target polynucleotide amplified by PCR from the genomic cellular DNA, and then sequenced.

Figure 6:
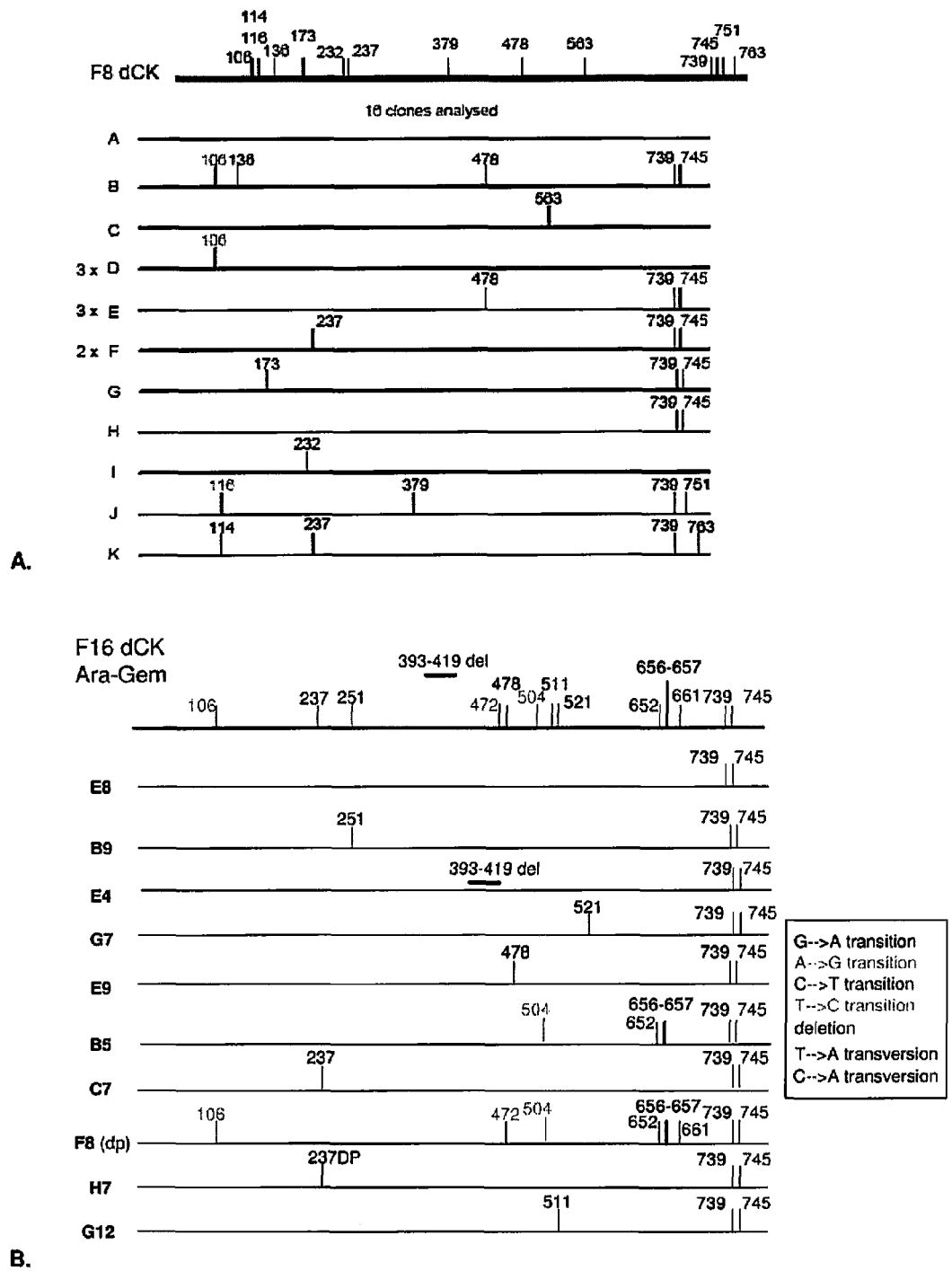
FIG. 6 is a diagram illustrating (A) sixteen (16) independent variants of the dCK target polynucleotide obtained at the F8 generation, and (B) 10 clones obtained at the F16 generation (B) using the method of the invention. At the top, the 14 positions that have been found modified in at least one of the 16 clones analysed are indicated by bars and their nucleotide position is given.

F8 generation. As shown in FIG. 6A, sixteen (16) independent clones from the F8 generation were analyzed. FIG. 6A shows, at the top, the fourteen (14) positions that have been found modified in at least one of the sixteen (16) clones analyzed, and their nucleotide position. Concerning the modification pattern of the clones analyzed, it is to be noted that when the same position is found in different clones, the same nucleotide substitution was involved. Certain positions indicate G to A transitions (114, 136, 232, 237, 379, 478, 563, 739, 751, 763), A to G transitions (106 and 116), C to A transversions (745), and deletion of one nucleotide (173). In this case, only one clone possessed the WT sequence (wild type sequence of the protein) (clone A), while the others contained from 1 to up to 5 nucleotide modifications, for a total of 10 different types of variants, and 14 positions of the gene that were modified. The pattern of modifications in the different clones is clearly indicative of the occurrence of frequent recombination between RNAs containing given sets of modifications. For instance clones B, E, F and H contain the same modifications in the same positions (positions 739 and 745) and it is extremely unlikely that these modifications have been originated independently. Interestingly, it seems that the first modifications, of these two, to arise was that at position 739 and that, before modifications 745 appeared, modifications 751 and 763 were generated (clones J and K, respectively) in a subpopulation of viruses that contained the 739 modifications.

These observations clearly indicate that recombination contributed to the diversification of the dCK gene during the procedure. Also the frequency of modifications found in this dataset is indicative of the occurrence of recombination, with a mutation rate of $2.4 \times 10^{-4}$ mutations detected per nt and per reverse transcription run, in line with the rate of recombination for HIV RT in cell culture that is of $3 \times 10^{-4}$/nt on average.

F16 generation. The evolution of the dCK gene has now been brought to the $17^{th}$ generation (F17). Sequencing of 10 clones of the F16 generation indicated the same mutation rate per nt and per reverse transcription run, as the results obtained at the F8 generation. The global mutation content of the population has therefore augmented since, by increasing the number of cycles, more reverse transcription runs have been performed. Thus, while 14 different modifications were found in 16 clones of the F8 generation, 15 modified positions have been observed in 10 clones at the F16 generation (FIG. 6B), meaning 0.8 mutations per clone in the F8 generation and 1.5 mutations per clone in the F16. More precisely, in the F8 generation 6.3 mutation combinations were found every 10 clones and in the F16 generation 10 combinations for 10 clones, indicating that the complexity of the population increases with the increase of the number of reverse transcription cycles. In FIG. 6B, the positions indicate G to A transitions (237, 478, 511, 521 and 739), A to G transitions (106 and 504), C to T transitions (625 and 661), a T to C transition (472), a C to A transversion (745), a T to A transversion (251) and a deletion of 27 nucleotides (939-419 del). Modification at positions 251, 393-419del, 472, 504, 511, 521, 625, 656-657 and 661 are new modified positions with respect to the modifications identified at the F8 generation.

This second set of analysis confirms the feasibility of the claimed method and the diversity generated in the sequence of the target polynucleotide.

Application of this Variant

Deoxynucleoside kinases are clinically relevant since they activate prodrugs used in antiviral and anticancer therapy, as for ganciclovir a compound used in about 10% of cancer gene therapy in clinical trials (Wiewrodt R., Amin K., Kiefer M., Jovanovic V. P., Kapoor V., et al. (2003) Cancer Gene Ther., 10: 353-64). Indeed a major problem in cell therapy is the possible uncontrolled proliferation of the genetically modified cells employed. If these cells also contained a gene that induced their suicide at drug concentrations at which wild type cells are not sensitive, they could be specifically removed by such a treatment. Similarly, these modified genes could be used in suicide gene therapy applications in cancer research by inducing a bystander effect.

The rationale of the approach is that cells transduced with dCK variants that might phosphorylate more efficiently pro-drugs could induce cell death at lower doses of pro-drugs than wild type dCK.

80 individual cellular clones at the F17 generation, obtained after transduction of 293T cells at a low multiplicity of infection (and therefore carrying a single variant of the target polynucleotide) have been isolated. The 80 clones have been tested for the kinetic of cell death induced after their exposal to different concentrations of the two anti-cancer drugs, AraC and Gemcitabine, which are cytidine analogues (the natural substrate of dCK) as follows.

Individual clones have been isolated after transduction of HEK 293T cells at low multiplicity of transduction (m.o.i.) and seeding of the transduced cells at limiting dilutions in 96-well plates. Individual cell clones growing in the presence of puromycin have then been expanded and seeded in parallel in several replicated 96-well plates. All these plates, with the exception of one to use as control, have been exposed to the anticancer drug at different concentrations, while the control plate has been maintained in the absence of drug. Seventy-two hours after exposure, cell death has been evaluated for each independent clone and for each drug treatment condition using the MTT assay (Promega) that is a colorimetric test used to quantify cell viability and proliferation. A relative rate of cell death has been calculated for each clone, with respect to the values observed in the plate where no drug was included. These values will then be compared to those observed for control clones. These controls have been constituted by three puro-resistant independent cell clones isolated after transduction with vectors carrying the wild type dCK enzyme. Three independent controls have been tested to consider that a potential variability might be present even with the same dCK sequence, due to possible epigenetic effects. The expression of the dCK gene could indeed be modulated by the position of integration of the proviral DNA within the target cell genome. For testing the potential epigenetic effect on the dCK variants, once a potential variant of interest has been identified, a retroviral vector containing the sequence of interest has been generated and several individual HEK-293T clones generated, isolated, and tested for the suicide phenotype.

Thus, the ability of the clones to phosphorylate anti-cancer and anti-viral drugs that are normally substrate of the human thymidine kinase, with a different efficiency than the wild type TK enzyme, has been tested.

Results on AraC

A curve of cell death observed in the presence of different concentrations of AraC on wild type 293T cells has been obtained.

A dCK variant (referred herein as G7, squares in FIG. 8) displayed a clear tendency to induce cell death at concentrations of the prodrug (AraC) for which cell death was much lower than the wt sequence (triangle in FIG. 8). The G7 variant has been demonstrated to contain a G to A transition at position 521, leading to the G174E variation at the amino acid level. For the TM mutant described by Sabini et al. (see Table 2 above), for which no effect on the efficiency of phosphorilation of AraC was observed in vitro, no significant difference was displayed with respect to the wt dCK enzyme. Interestingly, a frameshift variant generating a premature stop at the amino acid level was also identified (top curve in FIG. 8) indicating that this variant exerted a sort of effect of dominant negative with respect to the wt enzyme that is contained in the HEK 293T cells in which this assay was performed.

Results on Gemcitabine in HEK 293T Cells

The same approach has been followed for Gemcitabine. A dCK variant of interest has been identified (mutant G12), disclosing a G to A transition at position 511 (E171K at the amino acid level). The G12 variant induced cell death in a higher proportion of cells when tested at 10 nM Gemcitabine (the lowest concentration, among those tested, at which a differential effect was observed between G12 and the wt dCK) on twice as much cells than the dCK gene (ratio of cell survival in G12 cells/dCK cells: 0.50±0.11, average of 4 independent experiments). In the TM mutant (Table 2 above), this ratio was 0.89±0.08 (4 experiments).

Screening on dCK-Deficient Cells (Messa 10K Cells)

In order to obtain a stronger indication for the improved induction of cell death for dCK variants, we tested the 80 dCK variants (corresponding to the 80 clones obtained at the F17 generation) in a different cell line, the Messa 10K cells.

The Messa 10K cells are uterine sarcoma cells defective for the expression of the dCK gene (Jordheim L P, Galmarini C M, and Dumontet C, 2006). Due to the lack of a functional dCK protein, these cells display a high degree of resistance to the deoxycytidine analogues (Gemcitabine 1050: 11 uM) and are an ideal background in which to test the ability of the library of dCK variants to increase the sensitivity to Gemcitabine. Indeed, the phenotype produced by the introduction of a single copy of a dCK variant will be the result of this variant and would not be covered by the activity of several copies of wild type dCK.

Development of a Screening Methodology that Minimises Epigenetic Effects, in Sight of Screening of Libraries and of Therapeutic Intervention As previously mentioned above, the expression of the dCK gene variants could be modulated by the position of integration of the proviral DNA within the target cell genome, through epigenetic effects. These effects constitute a major problem for screening procedures, since they can lead to identification of false positive or to ignore interesting mutants. In addition, in sight of therapeutic approaches, it is essential to be able to use a vector/mutated gene combination that confer the desired phenotype to the cells target of the therapy, independently from epigenetic effects, since these are clearly unpredictable and might vary for each independent transduction procedure.

For these reasons, a strategy for the screening on Messa 10K cells (illustrated in FIG. 9) was set up, aiming at averaging the epigenetic effects possibly influencing the final phenotype by analysing a population of target cells containing the same dCK variant inserted in different sites of the genome. In brief, viral vectors or particles have been rescued from a subset of HEK293T isolated clones by transfection with transcomplementation plasmids and used, separately, to transduce Messa 10K cells, at a M.O.I.<1. Each transduction gave rise to 20-200 cellular clones, bearing the same dCK variant inserted in different parts of the genome. The totality of the clones of the same variant were cultivated and analysed for the sensitivity to Gemcitabine in the assay previously described. This approach allows to put in evidence the effect of the inserted sequence on the phenotype and to minimise epigenetic effects. This closely mimics what would happen in gene therapy, where a vector is needed that works efficiently on average, rather than a vector that works only in few cases where by chance the transgene is overexpressed.

Results on Gemcitabine on Messa 10K Cells

Four rounds of screening were performed on Messa 10K cells for a subset of dCK variants identified in the previous screening on HEK293T cells. Each experiment has confirmed the ability of G12 variants (previously described and identified in 293T cells) to induce cell death ratio higher than the one induced from a wild type dCK at a given Gemcitabine concentration (black solid lines versus dashed lines, FIG. 10A). For the other analysed variants, cell death curves were comparable to the curve given by wild type dCK (data not shown). At a 75 nM Gemcitabine concentration, G12 variant displayed a 90% cell death ratio while wild type dCK and other variants displayed 10 to 20% of maximal cell death (FIG. 10B).

A Western Blot (WB) analysis of cell lysates revealed that the phenotype of increased sensitivity to Gemcitabine was not due to an increase in protein production (FIG. 10C), but rather that the dCK G12 variant possibly has an improved ability in phosphorylating Gemcitabine. The WB also evidenced that Messa 10K cells (M) are able to produce some dCK proteins, possibly non functional. As the functional form of the kinase is a dimer, this explains why the cell death ratio in transduced cells never reaches 100%.

Phenotype Stability

The four rounds of screening on Messa 10K cells confirmed that the claimed method (retrovolution procedure) enables the isolation of a cell line (293T-G12-F16) producing viral vectors that, once inserted in human cells, confer a phenotype of increased sensitivity to Gemcitabine. The stability and reproducibility of the phenotype was verified by submitting the G12-F17 vectors or particles (rescued from G12-F16 cells) to a further passage: the viral vectors F17 were used to transduce fresh 293T cells to produce the 293T-G12 F17 cells, a new generation of vectors was produced by transfection with transcomplementation plasmids (G12-F18) and these were used to transduce Messa10K cells at low M.O.I. The analysis of the resulting Messa G12 F18 for the sensitivity to Gemcitabine confirmed that the phenotype is stable and transmissible (FIG. 11; black solid line and dark grey solid line).

Identification of Optimised Transgenes and Vectors for Expression in Producer Cells The repeated passages of the transgene in human cells, intrinsic to the claimed method, opened on the possibility of shaping the type of mutations generated in the transgene towards mutations "well-accepted" by human cells. The results presented here provide strong indications that this is actually ongoing during the claimed method. In particular, this was observed through (1) the progressive fixation in the cell population of two mutations in the dCK transgene, and (2) the convergence of all our lentiviral vectors towards the use of a specific U3 sequence (the one ensuring the expression of the genomic RNA) containing several mutations with respect to the starting sequence.

(1) Interestingly, during the evolution strategy (carried out by the claimed method), two mutations of the dCK gene have been found (739 G>A and 745 C>A), which are localised near the C-terminus of the protein, appeared first in a limited proportion of the mutants of the library (around 50% at the generation 8) and then became fixed in the whole population (100% at generation 16). This observation suggests that these mutations, although not influent for conferring the desired phenotype to the human cells (FIG. 10B, clone E8), somehow favoured the expansion of the viral vectors from which they are encoded and are probably better accepted for ectopic expression in the HEK 293T cells.

(2) During the retrovolution procedure, mutations are generated in regions of the viral RNA that undergoes retrotranscription. The sequencing of the proviral DNA region going from the 5'LTR to the end of the dCK gene revealed that all the analysed clones bear the same set of mutations in the U3 region of the LTR (FIG. 12). The same set of mutations is present in the global population of producer cells HEK 293T from generation F8 onward. These mutations likely result from natural selection occurring during evolution for the best-adapted variants of viral RNA, probably the variants expressing the highest content of genomic RNA. This observation suggests that this variant of the U3 promoter can be used to produce high titer viral vectors in human cells. All the clones, that have been sequenced, presented this variant of the U3 region, irrespective of the phenotype conferred to the target cell, indicating that this peculiarity of the U3 sequence had no influence on the screening procedure. This is expected, indeed, since the expression of the transgene is carried out from the EF1-alpha promoter and no expression of the transgene is expected to occur from the U3 promoter.

Finally, the subcloning of the G12 mutant from the cell line F16 and its insertion in a wild type lentiviral vector (the vector used for starting the whole procedure with the parental viruses) show that this G12 mutant maintains the ability to confer increased sensitivity to Gemcitabine to Messa 10K cells (FIG. 11; light grey solid line). This demonstrates that the backbone provided by the lentiviral vector did not influence the screening procedure.

Conclusions

From the implementation of the claimed method (retrovolution procedure), the following products were generated: 1) a HEK293T cell line (G12F16) producing viral vectors able to confer an increased sensitivity to Gemcitabine to the human cells. These cells evolve maintaining the capacity to produce vectors conferring the phenotype; 2) lentiviral derived vectors expressing a dCK variant able to reproducibly induce an increased sensitivity to Gemcitabine to human cells; and 3) A mutated vector backbone adapted for an improved replication and expression in human cells.

The above results show the interest of the methods of the invention to generate genetic diversity and to screen variants associated with a particular cell phenotype. A comparison of the variants obtained by the methods of the invention with variants obtained by different methods of the prior art have shown that results regarding protein activity observed in vitro are not necessarily observed when experiments are carried out in cell culture. The methods of the invention enable to bypass these drawbacks and to directly obtain variants with the desired activity in cells or desired effect on the phenotype of target cells.

EXAMPLE 2

Genetic Variability Generated in the Adaptor Protein SLP-76

Introduction

The evolution of SLP-76, an adaptor protein involved in signalling in response to T cell receptor activation, was also performed with the same procedure used for the dCK gene. The goal of targeting an adaptor protein is to provide an example of how our directed evolution system is adapted for studying the functionality of this important type of proteins. Indeed, activation of signalling pathways (as the lymphocyte differentiation pathway in which SLP-76 is involved) depends on several enzymes such as protein kinases and phosphatases, phospholipases, GTPases, but also on scaffolds and adaptors. These proteins are responsible for the recruitment of effectors in supra-molecular complexes, where the ordered activation of the various binding partners is regulated.

Analysis of scaffold and adaptor proteins function has been often carried out using gene knockout or overexpression. These approaches have provided useful information about the importance of these proteins but may be limited because either result in the complete impairment of lymphocyte differentiation and ability to mount an immune response or they completely alter the stochiometry of protein complexes, which may lead to misleading results. Directed mutagenesis of modular protein domains is starting to reveal, though, more discrete functions of these proteins, suggesting that cooperative effects are very important in the assembly of signalling protein complexes. Moreover, it appears that modifying the interaction of different effectors with scaffolds/adaptors may modulate the activation of specific signalling pathways. Indeed it has been shown that deregulated expression or mutations of these proteins can lead to development of lymphomas, leukaemias, autoimmune diseases or immunodeficiency.

It is evident that screening the activity of these proteins directly in the human cell is the most appropriate and most efficient approach one can follow due to the completeness of the screening system that limits the isolation of false positive molecules that can instead be frequent when simplified screening procedures are followed. The rationale of the screening procedure carried out by the inventors with the disclosed method is to detect variants that have defaults in signal transduction by monitoring the lack of activation of transcription in reporter cells where the NF-AT or interleukin 2 (IL-2) promoters drive the expression of the firefly luciferase gene. The activation of the IL-2 promoter and of the transcription factor NF-AT are two of the events that result from the signalling cascade regulated by SLP-76. In parallel, the activation of production and expression at the surface of the cell of the CD69 molecule (another event depending on the activation of the SLP-76 driven cascade) can also be followed. The goal is to find variants that are affected in at least one of the three readouts (NFAT— promoter-driven luc expression, IL-2-promoter-driven luc expression, and CD69 expression).

Differential effects on the three readouts would be an interesting result opening on the identification of mutations of SLP-76 that lead to a differential phenotype. This would be important for dissecting how the same adaptor can control differential activation pathways. Modification of this gene is expected to provide an example of the selection for negative phenotypes that our system allows (see FIG. 7) due to the possibility of first selecting cells containing a target polynucleotide through the selection for puromycin positive cells, followed by selection for a negative phenotype conferred by the target polynucleotide variant.

Two parts have been developed
  the generation of genetic variability in the SLP-76 gene; and
  the development of cellular tools (target cells) required for the analysis of the mutants of interest.

Generation of Genetic Variability in the SLP-76 Gene

Applying the same method as the one disclosed in example 1, but replacing the gene encoding the dCK gene by the target polynucleotide encoding the SLP-76 protein, the F9 generation has been reached. Nucleotide sequence of the SLP-76 gene and its corresponding protein sequence are disclosed in SEQ ID NO:3 and SEQ ID NO:4 respectively. Individual clones have been selected based on their Puro-resistant phenotype. Their sequence is currently being assessed.

Development of Cellular Tools

Concerning the cells needed for the screening of the mutants, cells having a negative genetic background (SLP-76−/−) but allowing the correct readout are required. SLP-76−/− cells were already available (Jurkat J14 cells SLP-76−/−). These cells allow screening based on the expression of CD69.

Concerning the screening based on the two luciferase-based readouts (either the one based on transcription driven by the NFAT or by IL2), the inventors have constructed two cell lines which as such are also part of the present invention:
  the Jurkat SLP-76−/−pIL2-luc cell clone, deposited at the CNCM (Paris, France) under accession number I-4236 on Oct. 30, 2009, in the name of Institut Pasteur, 25-28 rue du Docteur Roux, 75724 Paris Cedex 15, and resulting from the introduction in Jurkat J14 cells (SLP-76−/−) of the firefly luciferase gene under the control of two copies of the IL2 promoter; and
  the Jurkat SLP-76−/−NFAT-luc cell clone, deposited at the CNCM under accession number I-4237 on Oct. 30, 2009, in the name of Institut Pasteur, 25-28 rue du Docteur Roux, 75724 Paris Cedex 15, and resulting from the introduction in Jurkat J14 cells (SLP-76−/−) of the firefly luciferase gene preceded by three copies of the NFAT binding site.

These two clones have been shown to have a very low background luciferase level and a strong induction of luciferase transcription upon stimulation with Phorbol Myristate Acetate (PMA) and Calcimycine. Transduction into these cell clones of vectors containing the wild type SLP-76 gene has been shown to induce luciferase expression, thus opening the possibility of screening for SLP-76 variants.

After identification of the SLP-76 variants by sequencing, the IL-2-luc Jurkat cell lines and NFAT luc Jurkat cell lines are transduced with the SLP-76 particles from the library obtained by the disclosed method of the invention. After selecting, by limiting dilution of transduced cells, target cells having the Puror phenotype (resistance to puromycin), the induction of the expression of the luciferase is measured for each clone and compared to that observed in the presence of the wild type SLP-76 gene.

Once followed this approach with the SP-76 protein, other adaptors of signal transduction, involved in cancers, could be targeted. Library of mutants could for instance be generated and potentially made available in the context of a valorisation project.

EXAMPLE 3

Genetic Variability Generated in the Gene Encoding the Interferon Lambda

IFN λ exhibits several common features with type I IFNs since they share a signalling pathway involving the transcription factor ISGF3, driving the expression of a common set of responsive genes (Dumoutier L., Lejeune D., Hor S., Fickenscher H., Renauld J. C. (2003) Biochem. J. 370: 391-6; Kotenko S. V., Gallagher G., Baurin V. V., Lewis-Antes A., Shen M., et al. (2003) Nat. Immunol., 4: 69-77; and Sheppard P., Kindsvogel W., Xu W., Henderson K., Schlutsmeyer S., et al. (2003) Nat. Immunol., 4: 63-8). Consequently, IFN λ is able of establishing an antiviral state in sensitive cell lines and it possesses an antiproliferative activity (Meager A., Visvalingam K., Dilger P., Bryan D., Wadhwa M. (2005) Cytokine, 31: 109-18). IFN λ is of potential interest with respect to type I IFNs, due to the cell specific expression of their receptor in contrast to the ubiquitous presence of receptors for type I IFNs.

The method of the present invention is implemented to obtain variants with higher specific activities for the induction of ISGF3, especially on cells expressing low levels of IFN λ receptor. Two kinds of effects of variants of IFN λ are expected:

IFN λ variant having an increased efficiency that fully mimic type I IFNs; this kind of variant is useful in clinic to reduce the side effects of IFN therapy since the spectrum of responsive organs is restricted by the expression of the IFN λ receptor. This is interesting, for instance, for the treatment of HCV infections where a direct antiviral effect on hepatocytes (a cell type that expresses the IFN receptor) is wanted.

IFN λ variant behaving qualitatively like an ordinary type I IFN i.e., exhibiting antiviral, antiproliferative and Th1 driver bioactivity. It has recently been shown that IFNs are able to suppress hepatitis C viral replication in HuH-7 cells (Zhu H., Butera M., Nelson D. R., Liu C. (2005) Virol. J., 2: 80). It is conceivable that IFN variants could be of use in clinic to treat such a viral infection and the spectrum of responsive organs being restricted by the expression of IFNLR1, the treatment would be less likely to cause the myelosuppression and other side effects typically associated with type I IFN therapy (Brassard D. L., Grace M. J., Bordens R. W. (2002) J. Leukoc. Biol., 71: 565-81).

The method of the invention has now been implemented on the IFN λ target polynucleotide, and the fourth generation of viral particles has been reached. One possible problem that could have occur is the possible modification of the properties of the 293T cells once transduced by a vector that encodes for the IFN λ, since IFN λ has an antiviral activity. However, this problem has not been encountered for leading the successive steps of transfection and transduction, indicating that this is not the case.

Tests for the production of IFN λ have also been performed. Seventeen independent puro$^r$ clones (resistance to puromycin) have been isolated after transduction of 293T cells with parental particles, and expanded in 24-well plates. Cells have then been counted and seeded in new 24-wells plates at a homogeneous density. Forty-eight hours later, the supernatant was collected and applied on reporter HL116 cells seeded in a 96-well plate, at the same cell density in each well. HL116 cells are known to express the receptor for IFN λ and to possess a luciferase (luc) reporter gene under the control of an IFN type I inducible promoter. Thus, activation of the luc gene in these cells has been reported to be directly dependent on the avidity of the IFN λ for its receptor, and thus to reflect the functionality of the IFN λ or variants thereof, secreted by the transduced 293T cells.

In the experiments done by the inventors, activation of the luc expression system was observed, and at almost identical levels (variations in the order of 10-20%). The levels of luciferase expression observed in HL-116 exposed to the same amount of culture supernatant from the 17 independent clones (each tested in two independent experiments) are given in Table 3. Potential variations in the intensity of the luciferase activity observed in the reporter cells HL-116, would be therefore rather due to epigenetic effects linked to the integration site of the provirus, rather than to mutations.

TABLE 3 luciferase activity observed in HL-116 cells exposed to the culture supernatant from 17 independent clones isolated after transduction of 293T cells

| Clone | Luciferase average | Luc exp 1 | Luc exp 2 |
|---|---|---|---|
| 1 | 68.2 | 68.2 | 68.8 |
| 2 | 69.7 | 73.2 | 66.3 |
| 3 | 84.0 | 80.8 | 87.3 |
| 4 | 86.3 | 84.3 | 88.1 |
| 5 | 99.0 | 100.2 | 97.8 |
| 6 | 83.0 | 77.7 | 88.3 |
| 7 | 93.0 | 90.9 | 95.1 |
| 8 | 97.9 | 88.9 | 106.9 |
| 9 | 89.0 | 78.7 | 99.2 |
| 10 | 88.3 | 89.8 | 86.9 |
| 11 | 85.6 | 95.4 | 75.8 |
| 12 | 84.4 | 77.2 | 91.6 |
| 13 | 94.6 | 94.4 | 94.8 |
| 14 | 81.1 | 89.2 | 72.9 |
| 15 | 87.7 | 87.6 | 87.8 |
| 16 | 79.3 | 81.4 | 77.2 |
| 17 | 75.8 | 79.9 | 71.7 |

Finally, the intensity of activation found on HL116 is comparable for the supernatant of cells transduced with the parental generation, and with the F2 generation, indicating that no decrease in the production of IFN occurs by increasing the number of viral generations (data not shown). This example therefore demonstrates the successful use of the method of the invention to identify variants, of a target polynucleotide, involved in the desired phenotype.

These three examples demonstrate:

- that the method of the invention may be applied to genes of different nature (enzyme, adaptators, secreted proteins) to produce a library of cells expressing a diversity of variants of a target polynucleotide; and
- that these resulting variants may thus be easily isolated, according to the desired phenotype directly on target cells, by various methods (positive selection for a secreted protein, negative selection on a negative genetic background and positive selection on a negative genetic background).

BIBLIOGRAPHY

Anderson, J. P., R. Daifuku, and L. A. Loeb. 2004. Annual Review of Microbiology 58:183-205.

Brassard D L, Grace M J, Bordens R W. 2002. *J Leukoc Biol* 71: 565-81

Cannons J L, Yu L J, Hill B, Mijares L A, Dombroski D, et al. 2004. *Immunity* 21: 693-706

Daifuku, R. 2003. BioDrugs 17:169-177.

Das A T, Zhou X, Vink M, Klaver B, Verhoef K, et al. 2004. J Biol Chem 279: 18776-82

Dumoutier L, Lejeune D, Hor S, Fickenscher H, Renauld J C. 2003. Biochem J 370: 391-6

Harris, K., W. Brabant, S. Styrchak, A. Gall, and R. Daifuku. 2005 Antiviral Research 67:1-9.

Kotenko S V, Gallagher G, Baurin V V, Lewis-Antes A, et al. 2003. Nat Immunol 4: 69-77

Loeb, L., J. Essigmann, F. Kazazi, J. Zhang, K. Rose, and J. Mullins. 1999. Proceedings of the National Academy of Sciences of the United States of America 96:1492-1497.

Malissen B, Aguado E, Malissen M. 2005. Advances in Immunology 87: 1-25

Mansky L M. 1998. J Gen Virol 79 (Pt 6): 1337-45

Meager A, Visvalingam K, Dilger P, Bryan D, Wadhwa M. 2005. Cytokine 31: 109-18

Mennechet F J, Uze G. 2006. Blood

Sabini E, Ort S, Monnerjahn C, Konrad M, Lavie A. 2003. Nat Struct Biol 10: 513-9 353-64

Sheppard P, Kindsvogel W, Xu W, Henderson K, et al. 2003. Nat Immunol 4: 63-8

Wiewrodt R, Amin K, Kiefer M, Jovanovic V P, Kapoor V, et al. 2003. Cancer Gene Ther 10:

Yu X, Zhan X, D'Costa J, Tanavde V M, Ye Z, et al. 2003. Mol Ther 7: 827-38

Zhu H, Butera M, Nelson D R, Liu C. 2005. Virol J 2: 80

---

The invention claimed is:

1. An in vitro method of generating genetic diversity in a nucleotide sequence of a target polynucleotide, comprising:
   a) providing parental replication-defective lentiviral particles comprising a genetic material encapsidated in said particles, wherein said genetic material comprises at least one target polynucleotide and one or more regulatory elements necessary for transfer, transcription and optionally expression of said genetic material into a genome of a cell host;
   b) transducing producer cells with the parental replication-defective lentiviral particles of step a) to obtain parental producer cells containing integrated in their genome the nucleotide sequence of the target polynucleotide, optionally in the presence of a mutagen;
   c) transcomplementing the parental producer cells of step b) with viral proteins necessary for production of a first filial generation of replication-defective lentiviral particles (F1);
   d) collecting the first filial generation of replication-defective lentiviral particles (F1); and
   e) repeating, n consecutive times, with n being 1 or more, the following steps:
   e1) transducing fresh producer cells with the immediately previous filial generation of replication-defective lentiviral particles, optionally in the presence of a mutagen, thereby obtaining an Fn filial producer cell generation comprising cells containing integrated in their genome the nucleotide sequence of the target polynucleotide;
   e2) transcomplementing the Fn producer cells of step e1) with viral proteins necessary for production of an n+1 filial generation of replication-defective lentiviral particles (Fn+1); and
   e3) collecting the n+1 filial generation of replication-defective lentiviral particles (Fn+1);
   wherein transduction and integration of the nucleotide sequence of the target polynucleotide in the genome of the producer cells is independent from viral replication and results in clonal expansion of variants of the target polynucleotide,
   thereby, obtaining a population of replication-defective lentiviral particles of the n+1 filial generation, comprising particles that contain a nucleotide variant of the target polynucleotide.

2. The in vitro method of claim 1, wherein step e) further comprises before step e2), overtransducing m consecutive times, wherein m is at least 1, the transduced producer cells of step e1) with replication-defective lentiviral particles of the same immediately previous generation as the particles used in step e1), optionally in the presence of a mutagen.

3. The in vitro method of claim 1, wherein the transducing step b) and/or the transducing step e1) further comprises selecting for cells that have stably integrated in their genome the genetic material of the replication-defective lentiviral particles.

4. The in vitro method of claim 1, wherein the genetic material encapsidated in the replication-defective lentiviral particles is a nucleic acid comprising a 5' long terminal repeat (LTR), packaging sequences, the target polynucleotide, a regulatory element for driving the expression of said target polynucleotide, and a functional 3' LTR.

5. The in vitro method of claim 1, wherein the genetic material further comprises a central polypurine tract (cPPT) and a central termination sequence (CTS), in a flap forming sequence.

6. The in vitro method of claim 1, wherein said one or more regulatory element is a promoter driving the expression of the target polynucleotide.

7. The in vitro method of claim 6, wherein said genetic material further comprises at least one selectable marker gene, a cell surface marker, or a fluorescent marker, allowing selection of the cells transduced with the lentiviral particles of step a), and a second regulatory element for driving the expression of said at least one selectable marker gene.

8. The in vitro method of claim 7, wherein the second regulatory element is a promoter that is different from the promoter driving the expression of the target polynucleotide.

9. The in vitro method of claim 1, wherein the transcomplementation step comprises transfecting said producer cells with at least one plasmid, said plasmid capable of expressing in said producer cells, envelope proteins, and lentiviral Gag and Pol proteins.

10. The in vitro method of claim 1, wherein the replication-defective lentiviral particles comprise an envelope protein that is protein G of vesiculovirus (VSV-G).

11. The in vitro method of claim 1, wherein the producer cell is a mammalian cell.

12. The in vitro method of claim 1, wherein said at least one target polynucleotide encodes a protein.

13. The in vitro method of claim 6, wherein the promoter driving the expression of the target polynucleotide is selected from the group consisting of elongation factor 1-a promoter (EF1-a), CMV promoter, SV40 promoter, beta globin promoter and phosphoglycerate kinase (PGK) promoter.

14. The in vitro method of claim 8, wherein the promoter driving the expression of the at least one selectable marker gene is selected from the group consisting of elongation factor 1-a promoter (EF1-a), CMV promoter, SV40 promoter, beta globin promoter and phosphoglycerate kinase (PGK) promoter.

15. The in vitro method of claim 11, wherein the producer cells are 293T cells.

16. The in vitro method of claim 1, wherein said at least one target polynucleotide encodes a protein selected from the group consisting of structural proteins, functional proteins, enzymes and secreted proteins.

17. The in vitro method of claim 1, wherein the transcomplementation step comprises transfecting said producer cells with at least one plasmid configured to directly express in said producer cells in trans at least one protein selected from viral envelope proteins, Gag proteins and Pol proteins, wherein said at least one protein remedies the replication deficiency of the lentiviral particles.

18. The in vitro method of claim 17, wherein the transducing step b) and/or the transducing step e1) further comprises selecting for producer cells that have stably integrated in their genome the genetic material of the replication-defective lentiviral particles.

19. The in vitro method of claim 16, wherein the enzymes are kinases.

20. The in vitro method of claim 16, wherein the functional proteins are selected from the group consisting of pro-drug activation proteins, signal transduction proteins and receptor binding proteins.

21. The in vitro method according to claim 16, wherein the secreted proteins are interferons.

22. The in vitro method of claim 1, wherein said at least one target polynucleotide encodes the deoxycytidine kinase (dCK) as defined in SEQ ID NO: 2.

23. The in vitro method of claim 1, wherein said at least one target polynucleotide comprises SEQ ID NO: 1.

* * * * *

SEQUENCE LISTING

```
<160> NUMBER OF SEQ ID NOS: 6

<210> SEQ ID NO 1
<211> LENGTH: 783
<212> TYPE: DNA
<213> ORGANISM: Homo sapiens
<220> FEATURE:
<221> NAME/KEY: CDS
<222> LOCATION: (1)..(783)
<223> OTHER INFORMATION: dCK gene

<400> SEQUENCE: 1 atg gcc acc ccg ccc aag aga agc tgc ccg tct ttc tca gcc agc tct        48
Met Ala Thr Pro Pro Lys Arg Ser Cys Pro Ser Phe Ser Ala Ser Ser
1               5                   10                  15 gag ggg acc cgc atc aag aaa atc tcc atc gaa ggg aac atc gct gca        96
Glu Gly Thr Arg Ile Lys Lys Ile Ser Ile Glu Gly Asn Ile Ala Ala
                20                  25                  30 ggg aag tca aca ttt gtg aat atc ctt aaa caa ttg tgt gaa gat tgg       144
Gly Lys Ser Thr Phe Val Asn Ile Leu Lys Gln Leu Cys Glu Asp Trp
            35                  40                  45 gaa gtg gtt cct gaa cct gtt gcc aga tgg tgc aat gtt caa agt act       192
Glu Val Val Pro Glu Pro Val Ala Arg Trp Cys Asn Val Gln Ser Thr
        50                  55                  60 caa gat gaa ttt gag gaa ctt aca atg tct cag aaa aat ggt ggg aat       240
Gln Asp Glu Phe Glu Glu Leu Thr Met Ser Gln Lys Asn Gly Gly Asn
65                  70                  75                  80 gtt ctt cag atg atg tat gag aaa cct gaa cga tgg tct ttt acc ttc       288
Val Leu Gln Met Met Tyr Glu Lys Pro Glu Arg Trp Ser Phe Thr Phe
                85                  90                  95 caa aca tat gcc tgt ctc agt cga ata aga gct cag ctt gcc tct ctg       336
Gln Thr Tyr Ala Cys Leu Ser Arg Ile Arg Ala Gln Leu Ala Ser Leu
                100                 105                 110 aat ggc aag ctc aaa gat gca gag aaa cct gta tta ttt gaa cga            384
Asn Gly Lys Leu Lys Asp Ala Glu Lys Pro Val Leu Phe Phe Glu Arg
            115                 120                 125 tct gtg tat agt gac agg tat att ttt gca tct aat ttg tat gaa tct       432
Ser Val Tyr Ser Asp Arg Tyr Ile Phe Ala Ser Asn Leu Tyr Glu Ser
        130                 135                 140 gaa tgc atg aat gag aca gag tgg aca att tat caa gac tgg cat gac       480
Glu Cys Met Asn Glu Thr Glu Trp Thr Ile Tyr Gln Asp Trp His Asp
145                 150                 155                 160
```

```
tgg atg aat aac caa ttt ggc caa agc ctt gaa ttg gat gga atc att    528
Trp Met Asn Asn Gln Phe Gly Gln Ser Leu Glu Leu Asp Gly Ile Ile
            165                 170                 175 tat ctt caa gcc act cca gag aca tgc tta cat aga ata tat tta cgg    576
Tyr Leu Gln Ala Thr Pro Glu Thr Cys Leu His Arg Ile Tyr Leu Arg
        180                 185                 190 gga aga aat gaa gag caa ggc att cct ctt gaa tat tta gag aag ctt    624
Gly Arg Asn Glu Glu Gln Gly Ile Pro Leu Glu Tyr Leu Glu Lys Leu
        195                 200                 205 cat tat aaa cat gaa agc tgg ctc ctg cat agg aca ctg aaa acc aac    672
His Tyr Lys His Glu Ser Trp Leu Leu His Arg Thr Leu Lys Thr Asn
    210                 215                 220 ttc gat tat ctt caa gag gtg cct atc tta aca ctg gat gtt aat gaa    720
Phe Asp Tyr Leu Gln Glu Val Pro Ile Leu Thr Leu Asp Val Asn Glu
225                 230                 235                 240 gac ttt aaa gac aaa tat gaa agt ctg gtt gaa aag gtc aaa gag ttt    768
Asp Phe Lys Asp Lys Tyr Glu Ser Leu Val Glu Lys Val Lys Glu Phe
                245                 250                 255 ttg agt act ttg tga                                                783
Leu Ser Thr Leu
            260

<210> SEQ ID NO 2
<211> LENGTH: 260
<212> TYPE: PRT
<213> ORGANISM: Homo sapiens

<400> SEQUENCE: 2

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
    50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Ala Cys Leu Ser Arg Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Asp Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220
```

```
Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
            245                 250                 255

Leu Ser Thr Leu
        260

<210> SEQ ID NO 3
<211> LENGTH: 1632
<212> TYPE: DNA
<213> ORGANISM: Homo sapiens
<220> FEATURE:
<221> NAME/KEY: CDS
<222> LOCATION: (1)..(1632)
<223> OTHER INFORMATION: SLP-76 gene

<400> SEQUENCE: 3 atg gac tac aaa gac gac gac gac aaa gga tcc gca ctg agg aat gtg      48
Met Asp Tyr Lys Asp Asp Asp Asp Lys Gly Ser Ala Leu Arg Asn Val
1               5                   10                  15 ccc ttt cgc tca gag gtc ctg ggc tgg gac ccc gac agc ctt gct gac      96
Pro Phe Arg Ser Glu Val Leu Gly Trp Asp Pro Asp Ser Leu Ala Asp
                20                  25                  30 tat ttc aag aag ctc aac tat aag gac tgt gag aag gca gtg aag aag     144
Tyr Phe Lys Lys Leu Asn Tyr Lys Asp Cys Glu Lys Ala Val Lys Lys
            35                  40                  45 tac cac atc gat ggg gct cgc ttc ttg aac ctg aca gaa aat gac atc     192
Tyr His Ile Asp Gly Ala Arg Phe Leu Asn Leu Thr Glu Asn Asp Ile
        50                  55                  60 cag aag ttc ccc aag ctc cgg gtg ccg att ctc agt aag tta agt cag     240
Gln Lys Phe Pro Lys Leu Arg Val Pro Ile Leu Ser Lys Leu Ser Gln
65              70                  75                  80 gaa atc aac aag aac gaa gag agg agg agc atc ttc aca cgc aaa ccc     288
Glu Ile Asn Lys Asn Glu Glu Arg Arg Ser Ile Phe Thr Arg Lys Pro
                85                  90                  95 caa gtc ccg cgg ttt cct gaa gag aca gaa agc cac gaa gag gac aat     336
Gln Val Pro Arg Phe Pro Glu Glu Thr Glu Ser His Glu Glu Asp Asn
                100                 105                 110 ggg ggc tgg tcg tcc ttt gaa gaa gac gat tat gaa agt ccc aat gat     384
Gly Gly Trp Ser Ser Phe Glu Glu Asp Asp Tyr Glu Ser Pro Asn Asp
            115                 120                 125 gac cag gat ggg gag gat gat gga gac tat gag tcc ccc aat gag gag     432
Asp Gln Asp Gly Glu Asp Asp Gly Asp Tyr Glu Ser Pro Asn Glu Glu
        130                 135                 140 gaa gag gca ccc gtg gaa gat gac gcg gat tat gag ccg cca ccc tcc     480
Glu Glu Ala Pro Val Glu Asp Asp Ala Asp Tyr Glu Pro Pro Pro Ser
145                 150                 155                 160 aat gac gag gaa gct ctg cag aac tcc atc ctg cct gcc aag cct ttc     528
Asn Asp Glu Glu Ala Leu Gln Asn Ser Ile Leu Pro Ala Lys Pro Phe
                165                 170                 175 ccc aac tcc aac tcc atg tac atc gac cgg ccc ccc tct ggg aaa acc     576
Pro Asn Ser Asn Ser Met Tyr Ile Asp Arg Pro Pro Ser Gly Lys Thr
                180                 185                 190 ccc cag cag cct cct gtg ccc ccc cag aga ccg atg gcc gcc ctc ccg     624
Pro Gln Gln Pro Pro Val Pro Pro Gln Arg Pro Met Ala Ala Leu Pro
            195                 200                 205 ccc cca cca gcc ggc cgg aat cac tcg cca ctg ccc cca ccc cag acc     672
Pro Pro Pro Ala Gly Arg Asn His Ser Pro Leu Pro Pro Pro Gln Thr
        210                 215                 220 aac cac gaa gaa ccc agc aga agc aga aac cac aaa acg gca aag ctt     720
Asn His Glu Glu Pro Ser Arg Ser Arg Asn His Lys Thr Ala Lys Leu
```

```
                225                 230                 235                 240
cct gct cct tca ata gac aga agc acg aaa cct ccc cta gat cgt tca      768
Pro Ala Pro Ser Ile Asp Arg Ser Thr Lys Pro Pro Leu Asp Arg Ser
                245                 250                 255 tta gct ccg ttt gat aga gaa ccc ttc aca cta gga aag aaa cca cca      816
Leu Ala Pro Phe Asp Arg Glu Pro Phe Thr Leu Gly Lys Lys Pro Pro
            260                 265                 270 ttt tct gac aag ccc tcg att cca gcg gga agg tca ctc ggg gag cat      864
Phe Ser Asp Lys Pro Ser Ile Pro Ala Gly Arg Ser Leu Gly Glu His
        275                 280                 285 tta ccc aag att caa aag cct cct tta cca ccg acc acg gaa aga cat      912
Leu Pro Lys Ile Gln Lys Pro Pro Leu Pro Pro Thr Thr Glu Arg His
    290                 295                 300 gaa agg agc agc ccc ctg cca ggg aag aag cca cct gtg cca aag cat      960
Glu Arg Ser Ser Pro Leu Pro Gly Lys Lys Pro Pro Val Pro Lys His
305                 310                 315                 320 gga tgg gga cca gac agg aga gag aat gat gaa gat gat gtg cat caa     1008
Gly Trp Gly Pro Asp Arg Arg Glu Asn Asp Glu Asp Asp Val His Gln
                325                 330                 335 aga cct ttg ccc cag cca gca cta ctt cct atg agc tcc aac act ttc     1056
Arg Pro Leu Pro Gln Pro Ala Leu Leu Pro Met Ser Ser Asn Thr Phe
            340                 345                 350 cct tca gga tct act aag cca agt ccc atg aac cct ctc cca tcc tct     1104
Pro Ser Gly Ser Thr Lys Pro Ser Pro Met Asn Pro Leu Pro Ser Ser
        355                 360                 365 cac atg cct gga gca ttc tca gaa agt aac agc agt ttt cca cag agt     1152
His Met Pro Gly Ala Phe Ser Glu Ser Asn Ser Ser Phe Pro Gln Ser
    370                 375                 380 gcc tcc ctg cca cca tac ttc tct caa ggc cct agc aac aga cca cct     1200
Ala Ser Leu Pro Pro Tyr Phe Ser Gln Gly Pro Ser Asn Arg Pro Pro
385                 390                 395                 400 atc aga gcc gaa ggc aga aac ttc ccc ttg cca ctt cca aac aaa cct     1248
Ile Arg Ala Glu Gly Arg Asn Phe Pro Leu Pro Leu Pro Asn Lys Pro
                405                 410                 415 cgg ccc cca tcc ccc gcg gag gaa gag aat tca tta aat gaa gag tgg     1296
Arg Pro Pro Ser Pro Ala Glu Glu Glu Asn Ser Leu Asn Glu Glu Trp
            420                 425                 430 tac gtt tct tat att acc cga cca gag gca gaa gct gct ctt aga aag     1344
Tyr Val Ser Tyr Ile Thr Arg Pro Glu Ala Glu Ala Ala Leu Arg Lys
        435                 440                 445 ata aac cag gat ggc aca ttt ctg gtc aga gac agc tct aaa aaa aca     1392
Ile Asn Gln Asp Gly Thr Phe Leu Val Arg Asp Ser Ser Lys Lys Thr
    450                 455                 460 aca acc aat cca tat gtc ctc atg gtg ttg tac aaa gat aaa gtt tac     1440
Thr Thr Asn Pro Tyr Val Leu Met Val Leu Tyr Lys Asp Lys Val Tyr
465                 470                 475                 480 aac atc cag atc cgt tat cag aag gaa agt caa gtt tac ttg ttg gga     1488
Asn Ile Gln Ile Arg Tyr Gln Lys Glu Ser Gln Val Tyr Leu Leu Gly
                485                 490                 495 act gga ctc cga ggg aaa gag gac ttt ctg tct gtg tca gat att att     1536
Thr Gly Leu Arg Gly Lys Glu Asp Phe Leu Ser Val Ser Asp Ile Ile
            500                 505                 510 gac tac ttc agg aaa atg cca ctt ctg ctc att gat ggg aaa aac cga     1584
Asp Tyr Phe Arg Lys Met Pro Leu Leu Leu Ile Asp Gly Lys Asn Arg
        515                 520                 525 ggt tcc aga tac cag tgc aca tta acg cat gct gca ggg tac cca tag     1632
Gly Ser Arg Tyr Gln Cys Thr Leu Thr His Ala Ala Gly Tyr Pro
    530                 535                 540
```

```
<210> SEQ ID NO 4
<211> LENGTH: 543
<212> TYPE: PRT
<213> ORGANISM: Homo sapiens

<400> SEQUENCE: 4

Met Asp Tyr Lys Asp Asp Asp Lys Gly Ser Ala Leu Arg Asn Val
1               5                   10                  15

Pro Phe Arg Ser Glu Val Leu Gly Trp Asp Pro Asp Ser Leu Ala Asp
            20                  25                  30

Tyr Phe Lys Lys Leu Asn Tyr Lys Asp Cys Glu Lys Ala Val Lys Lys
                35                  40                  45

Tyr His Ile Asp Gly Ala Arg Phe Leu Asn Leu Thr Glu Asn Asp Ile
    50                  55                  60

Gln Lys Phe Pro Lys Leu Arg Val Pro Ile Leu Ser Lys Leu Ser Gln
65                  70                  75                  80

Glu Ile Asn Lys Asn Glu Glu Arg Arg Ser Ile Phe Thr Arg Lys Pro
                85                  90                  95

Gln Val Pro Arg Phe Pro Glu Glu Thr Glu Ser His Glu Glu Asp Asn
            100                 105                 110

Gly Gly Trp Ser Ser Phe Glu Glu Asp Asp Tyr Glu Ser Pro Asn Asp
        115                 120                 125

Asp Gln Asp Gly Glu Asp Asp Gly Asp Tyr Glu Ser Pro Asn Glu Glu
    130                 135                 140

Glu Glu Ala Pro Val Glu Asp Asp Ala Asp Tyr Glu Pro Pro Pro Ser
145                 150                 155                 160

Asn Asp Glu Glu Ala Leu Gln Asn Ser Ile Leu Pro Ala Lys Pro Phe
                165                 170                 175

Pro Asn Ser Asn Ser Met Tyr Ile Asp Arg Pro Pro Ser Gly Lys Thr
            180                 185                 190

Pro Gln Gln Pro Pro Val Pro Pro Gln Arg Pro Met Ala Ala Leu Pro
        195                 200                 205

Pro Pro Pro Ala Gly Arg Asn His Ser Pro Leu Pro Pro Pro Gln Thr
    210                 215                 220

Asn His Glu Glu Pro Ser Arg Ser Arg Asn His Lys Thr Ala Lys Leu
225                 230                 235                 240

Pro Ala Pro Ser Ile Asp Arg Ser Thr Lys Pro Pro Leu Asp Arg Ser
                245                 250                 255

Leu Ala Pro Phe Asp Arg Glu Pro Phe Thr Leu Gly Lys Lys Pro Pro
            260                 265                 270

Phe Ser Asp Lys Pro Ser Ile Pro Ala Gly Arg Ser Leu Gly Glu His
        275                 280                 285

Leu Pro Lys Ile Gln Lys Pro Pro Leu Pro Pro Thr Thr Glu Arg His
    290                 295                 300

Glu Arg Ser Ser Pro Leu Pro Gly Lys Lys Pro Pro Val Pro Lys His
305                 310                 315                 320

Gly Trp Gly Pro Asp Arg Arg Glu Asn Asp Glu Asp Val His Gln
                325                 330                 335

Arg Pro Leu Pro Gln Pro Ala Leu Leu Pro Met Ser Ser Asn Thr Phe
            340                 345                 350

Pro Ser Gly Ser Thr Lys Pro Ser Pro Met Asn Pro Leu Pro Ser Ser
        355                 360                 365

His Met Pro Gly Ala Phe Ser Glu Ser Asn Ser Ser Phe Pro Gln Ser
    370                 375                 380
```

```
Ala Ser Leu Pro Pro Tyr Phe Ser Gln Gly Pro Ser Asn Arg Pro Pro
385                 390                 395                 400

Ile Arg Ala Glu Gly Arg Asn Phe Pro Leu Pro Leu Pro Asn Lys Pro
            405                 410                 415

Arg Pro Pro Ser Pro Ala Glu Glu Asn Ser Leu Asn Glu Glu Trp
            420                 425                 430

Tyr Val Ser Tyr Ile Thr Arg Pro Glu Ala Glu Ala Leu Arg Lys
            435                 440                 445

Ile Asn Gln Asp Gly Thr Phe Leu Val Arg Asp Ser Ser Lys Lys Thr
        450                 455                 460

Thr Thr Asn Pro Tyr Val Leu Met Val Leu Tyr Lys Asp Lys Val Tyr
465                 470                 475                 480

Asn Ile Gln Ile Arg Tyr Gln Lys Glu Ser Gln Val Tyr Leu Leu Gly
            485                 490                 495

Thr Gly Leu Arg Gly Lys Glu Asp Phe Leu Ser Val Ser Asp Ile Ile
            500                 505                 510

Asp Tyr Phe Arg Lys Met Pro Leu Leu Leu Ile Asp Gly Lys Asn Arg
            515                 520                 525

Gly Ser Arg Tyr Gln Cys Thr Leu Thr His Ala Ala Gly Tyr Pro
        530                 535                 540

<210> SEQ ID NO 5
<211> LENGTH: 635
<212> TYPE: DNA
<213> ORGANISM: Artificial
<220> FEATURE:
<223> OTHER INFORMATION: wild-type HIV-1 LTR

<400> SEQUENCE: 5
tggaagggct aattcactcc caaagaagac aagatatcct tgatctgtgg atctaccaca        60
cacaaggcta cttccctgat tagcagaact acacaccagg ccagggggtc agatatccac       120
tgacctttgg atggtgctac aagctagtac cagttgagcc agataaggta gaagaggcca      180
ataaaggaga gaacaccagc ttgttacacc ctgtgagcct gcatgggatg gatgacccgg      240
agagagaagt gttagagtgg aggtttgaca gccgcctagc atttcatcac gtggcccgag      300
agctgcatcc ggagtacttc aagaactgct gatatcgagc ttgctacaag ggactttccg      360
ctggggactt tccagggagg cgtggcctgg gcgggactgg ggagtggcga gccctcagat      420
cctgcatata agcagctgct ttttgcctgt actgggtctc tctggttaga ccggatctga      480
gcctgggagc tctctggcta actagggaac ccactgctta agcctcaata aagcttgcct      540
tgagtgcttc aagtagtgtg tgcccgtctg ttgtgtgact ctggtaacta gagatccctc      600 agacccttt agtcagtgtg aaaaatctc tagca                                  635

<210> SEQ ID NO 6
<211> LENGTH: 635
<212> TYPE: DNA
<213> ORGANISM: Artificial
<220> FEATURE:
<223> OTHER INFORMATION: mutated HIV-1 LTR

<400> SEQUENCE: 6
tggaagggct aattcactcc caaggaagac aagatatcct tgatctgtgg atctaccaca       60
cacaaggcta cttccctgat tggcagaact acacaccagg ccagggatc agatatccac      120 tgacctttgg atggtgctac aagctagtac cagttgagca agagaaggta gaagaagcca    180
atgaaggaga gaacacccgc ttgttacacc ctgtgagcct gcatgggatg gatgacccgg    240
```

```
agagagaagt attagagtgg aggtttgaca gccgcctagc atttcatcac atggcccgag      300
agctgcatcc ggagtacttc aagaactgct gacatcgagc ttgctacaag ggactttccg      360
ctggggactt tccagggagg cgtggcctgg gcgggactgg ggagtggcga gccctcagat      420
gctgcatata agcagctgct ttttgcttgt actgggtctc tctggttaga ccggatctga      480
gcctgggagc tctctggcta actagggaac ccactgctta agcctcaata aagcttgcct      540
tgagtgcttc aagtagtgtg tgcccgtctg ttgtgtgact ctggtaacta gagatccctc      600 agacccttt agtcagtgtg gaaaaatctc tagca                                  635
```